US008235984B2

(12) United States Patent
Swoyer et al.

(10) Patent No.: US 8,235,984 B2
(45) Date of Patent: Aug. 7, 2012

(54) TUNA DEVICE WITH INTEGRATED SALINE RESERVOIR

(75) Inventors: John M. Swoyer, Andover, MN (US); Yelena G. Tropsha, Plymouth, MN (US); Julie M. Woessner, St. Paul, MN (US); Mark A. Christopherson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1279 days.

(21) Appl. No.: 11/950,751

(22) Filed: Dec. 5, 2007

(65) Prior Publication Data

US 2008/0077125 A1    Mar. 27, 2008

Related U.S. Application Data

(62) Division of application No. 10/915,310, filed on Aug. 10, 2004, now Pat. No. 7,322,974.

(51) Int. Cl.
*A61B 18/14* (2006.01)
(52) U.S. Cl. .............................. 606/41; 607/105; 606/48
(58) Field of Classification Search .................... 606/41, 606/45–50; 607/101–105
See application file for complete search history.

(56) References Cited

U.S. PATENT DOCUMENTS

| | | | |
|---|---|---|---|
| 4,696,684 A | | 9/1987 | Shen |
| 5,334,193 A | | 8/1994 | Nardella |
| 5,370,675 A | | 12/1994 | Edwards et al. |
| 5,609,573 A | * | 3/1997 | Sandock ......................... 604/22 |
| 5,685,877 A | * | 11/1997 | Pagedas et al. ................. 606/46 |
| 5,762,626 A | | 6/1998 | Lundquist et al. |
| 5,964,756 A | | 10/1999 | McGaffigan et al. |
| 6,063,081 A | * | 5/2000 | Mulier et al. ................... 606/45 |
| 6,238,393 B1 | | 5/2001 | Mulier et al. |
| 6,302,903 B1 | | 10/2001 | Mulier et al. |
| 6,315,777 B1 | * | 11/2001 | Comben ......................... 606/41 |
| 6,328,393 B1 | | 12/2001 | Lin et al. |
| 6,409,722 B1 | | 6/2002 | Hoey et al. |
| 6,428,538 B1 | | 8/2002 | Blewett et al. |

(Continued)

FOREIGN PATENT DOCUMENTS

WO          03/005918          1/2003

(Continued)

OTHER PUBLICATIONS

European Search Report issued for co-pending EP Application No. 05784963.0; Jul. 29, 2009; 6 pages.

(Continued)

*Primary Examiner* — Michael Peffley

(57) ABSTRACT

Methods and apparatus for ablating a target tissue are discussed. Such methods and apparatus include those that simplify tissue ablation. For example, a tissue ablation device having an actuator, such as a trigger mechanism, coupled to a power source and an electrode is discussed. A single step of engaging the actuator causes the electrode to be introduced into the target tissue and causes energy to be delivered from the power supply to the tissue via the electrode. By way of additional example, a tissue ablation device having an actuator coupled to a fluid source and an electrode is discussed. A single step of engaging the actuator causes conductive fluid to flow from the fluid source to the target tissue location and causes the electrode to be introduced to the target tissue location. The fluid source may be a conductive fluid, such as saline, which may increase the efficiency of ablation. Various other configurations and methods that simplify tissue ablation are also discussed.

17 Claims, 18 Drawing Sheets

U.S. PATENT DOCUMENTS

| | | |
|---|---|---|
| 6,494,902 B2 | 12/2002 | Hoey et al. |
| 6,497,705 B2 | 12/2002 | Comben |
| 6,526,320 B2 | 2/2003 | Mitchell |
| 6,537,248 B2 | 3/2003 | Mulier et al. |
| 6,537,272 B2 | 3/2003 | Christopherson et al. |
| 6,623,515 B2 | 9/2003 | Mulier et al. |
| 2001/0025178 A1 | 9/2001 | Mulier et al. |
| 2001/0041921 A1 | 11/2001 | Mulier et al. |
| 2002/0019628 A1 | 2/2002 | Comben |
| 2002/0035387 A1 | 3/2002 | Mulier et al. |
| 2002/0049439 A1 | 4/2002 | Mulier et al. |
| 2002/0058933 A1 | 5/2002 | Christopherson et al. |
| 2002/0058935 A1 | 5/2002 | Hoey et al. |
| 2002/0151884 A1 | 10/2002 | Hoey et al. |
| 2002/0183733 A1 | 12/2002 | Mulier et al. |
| 2003/0073989 A1 | 4/2003 | Hoey et al. |
| 2004/0133197 A1 | 7/2004 | Utley et al. |

FOREIGN PATENT DOCUMENTS

| | | |
|---|---|---|
| WO | 03/047446 | 6/2003 |

OTHER PUBLICATIONS

Final office action for U.S. Appl. No. 11/573,417, mailed Jan. 13, 2012, 9 pages.

Response to the final office action for U.S. Appl. No. 11/573,417, filed Apr. 13, 2012, 27 pages.

* cited by examiner

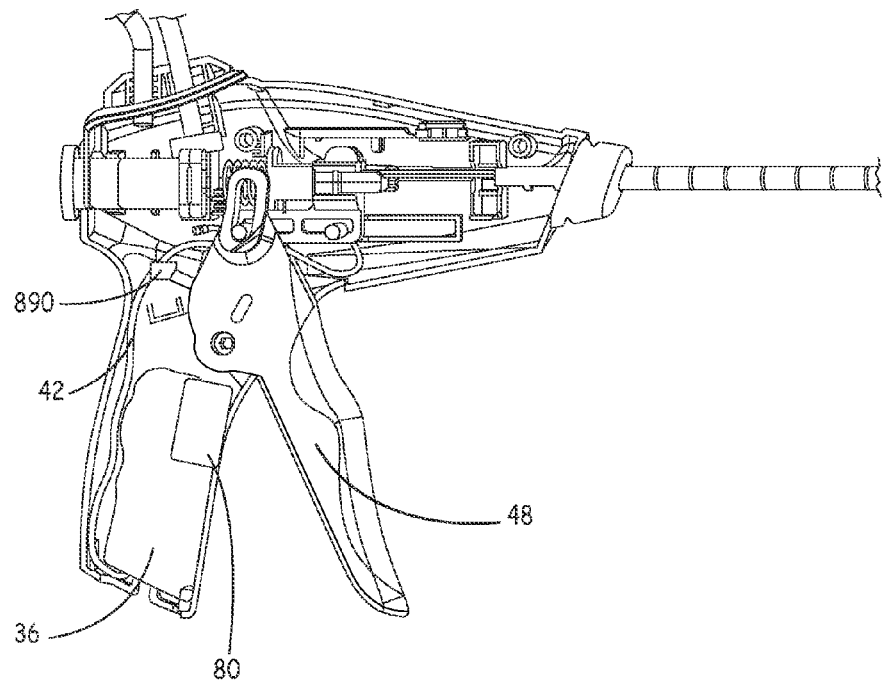
FIG. 11A
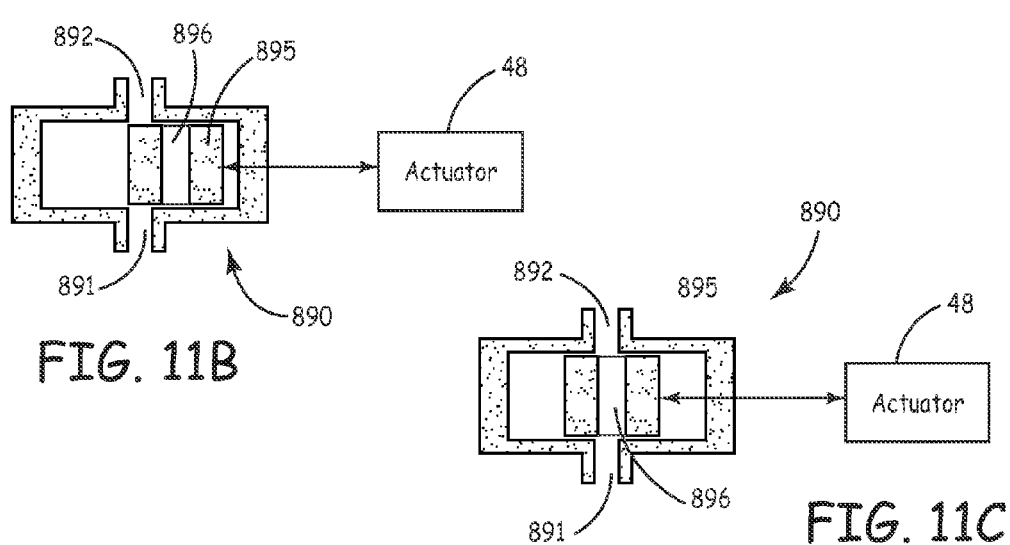
FIG. 11B
FIG. 11C

TUNA DEVICE WITH INTEGRATED SALINE RESERVOIR

CROSS-REFERENCE

This application is a divisional of U.S. patent application Ser. No. 10/915,310, filed Aug. 10, 2004, issued as U.S. Pat. No. 7,322,974 on Jan. 29, 2008. The entire content of this application is incorporated herein by reference.

FIELD

This disclosure relates to methods and apparatus for ablating tissue, such as Trans-Urethral Needle Ablation (TUNA) devices, including methods and apparatus for performing tissue ablating procedures with a wet or virtual electrode.

BACKGROUND

In recent history, tissue ablation procedures have employed a "dry" electrode. Dry electrode tissue ablation systems, such as TUNA systems, typically have needle electrodes coupled to a trigger mechanism for deploying the needles. The needles are coupled to a power generator. A manual switch is typically engaged to complete a circuit allowing ablative energy to flow from the power generator to the tissue via the needles. Thus, for a typical tissue ablation device to deliver ablative energy to a tissue, an end use of the device performs at least two separate steps: 1) engaging a trigger mechanism to deploy needles and 2) engaging a switch to supply ablative energy from the power generator to the tissue via the needles. More simplified systems have not been described.

Rather, more complex systems in the form of "wet" electrode systems have been proposed. While more complex, wet electrode systems have been proposed to address some shortcomings of dry electrode systems. More particularly, the amount of power delivered and speed of lesion formation in dry electrode approaches is limited by high impedance at the electrode-tissue interface. To minimize this issue, it has been proposed to pump saline through the electrode to create a "wet" electrode. Saline increases the conductivity of the tissue to be treated, allowing for increased efficiency of tissue ablation. However, proposed wet electrode tissue ablation systems may require additional controls and equipment for delivering the saline, making wet electrode tissue ablation, such as TUNA, more complex to perform than traditional dry electrode tissue ablation.

BRIEF SUMMARY

An embodiment of the invention provides a method for ablating tissue at a target location. The method comprises introducing an electrode into the target location and applying an ablative energy to the tissue via the electrode. The electrode is introduced to the target location and the ablative energy is applied to the tissue through a single step carried out by a user of a system capable of introducing the electrode and applying the ablative energy. In various embodiments, the single step comprises engaging an actuator of the system. The system may be, for example, a TUNA system. The method may further comprise introducing a conductive fluid to the target location. The conductive fluid may be introduced in the single step, which may be engaging an actuator.

In an embodiment, the invention provides a system for ablating a target tissue at a target location. The device comprises an actuator operably coupled an electrode and an energy source. The energy source is operably coupled to the electrode. The actuator is configured to cause the electrode to enter the target tissue and to cause the energy source to deliver ablative energy to the tissue via the electrode. The system may further comprise a fluid source. The actuator may be configured to cause fluid from the fluid source to flow to the target tissue.

An embodiment of the invention provides a method for ablating tissue at a target location. The method comprises introducing an electrode into the target location and introducing a conductive fluid to the target location. The electrode and the conductive fluid are introduced into the target location through a single step carried out by a user of a system capable of introducing the electrode and the conductive fluid. In various embodiments, the single step comprises engaging an actuator of the system. The system may be, for example, a TUNA system. The method further comprises applying energy to the target location via the electrode to ablate the tissue.

In an embodiment, the invention provides a system or device for ablating a target tissue at a target location. The system or device comprises an actuator operably coupled to a fluid source and an electrode. The actuator is configured to cause the electrode to enter the target tissue and to cause fluid from the fluid source to flow to the target tissue. The fluid source may be contained within the device, external to the device, or a combination thereof.

An embodiment of the invention provides a device for ablating a tissue at a target location. The device comprises a housing and an elongate probe member extending from the housing. The elongate probe member comprises proximal and distal ends and is provided with a passageway extending at least substantially from the proximal end to the distal end. The device further comprises an ablation needle. The ablation needle comprises proximal and distal ends and a lumen extending at least substantially from the proximal end to the distal end. The ablation needle is slidably disposed within the passageway of the elongate probe member. The device may optionally comprise a sheath. The sheath has proximal and distal ends and a lumen extending at least substantially between the proximal and distal ends. The sheath may be slidably disposed within the passageway of the elongate probe member. The needle may be slidably disposed within the lumen of the sheath. The device further comprises a reservoir capable of holding a conductive fluid. The reservoir is in fluid communication with one or more of the lumen of the sheath, the lumen of the needle, or the passageway of the elongate probe member. The device further comprises an actuator. The actuator is operably coupled to the reservoir and configured to cause the conductive fluid to flow through one or more of the lumen of the sheath, the lumen of the first needle, or the first passageway of the elongate tubular member into the target location. The actuator is also operably coupled to the proximal end of the first needle, and optionally the sheath, and configured to cause the distal end of the first needle, and optionally the sheath, to extend into the target location. In an embodiment, the device may further comprise a discharge member. The discharge member comprises proximal and distal portions. The proximal portion of the discharge member is in fluid communication with the reservoir, and the distal portion of the discharge member is in fluid communication with one or more of the lumen of the sheath, the lumen of the first needle, or the first passageway of the elongate probe member. The discharge member is coupled to the actuator such that engaging the actuator forces the conductive fluid to flow from the discharge member to the target location through one or both of the lumen of the first needle or the first passageway of the elongate probe member. The discharge member may also be coupled to the actuator such that disengaging the actuator reduces pressure in the discharge member relative to the reservoir, allowing the conductive fluid from the reservoir to be drawn into the discharge member.

An embodiment of the invention provides a device for ablating a tissue at a target location. The device comprises a housing and an elongate probe member extending from the housing. The elongate probe member has proximal and distal ends and is provided with a passageway extending at least substantially from the proximal end to the distal end. The device further comprises an ablation needle. The ablation needle comprises proximal and distal ends and a lumen extending at least substantially from the proximal end to the distal end. The needle is slidably disposed within the passageway of the elongate probe member. The device may optionally comprise a sheath. The sheath has proximal and distal ends and a lumen extending at least substantially between the proximal and distal ends. The sheath may be slidably disposed within the passageway of the elongate probe member. The needle may be slidably disposed within the lumen of the sheath. The device further comprises a tubular member comprising a lumen and adapted to permit flow of a conductive fluid. The device further comprises a valve having a proximal portion and a distal portion. The proximal portion of the valve is in fluid communication with the lumen of the tubular member, and the distal portion of the valve is in fluid communication with one or more of the lumen of the sheath, the lumen of the needle, or the passageway of the elongate probe member. The valve is configured to be moved between an open position and a closed position. The open position allows conductive fluid flow from the lumen of the tubular member to one or more of the lumen of the sheath, the lumen of the needle, or the passageway of the elongate probe member. The closed position prevents fluid flow from the lumen of the tubular member to one or more of the lumen of the sheath, the lumen of the needle, or the passageway of the elongate probe member. The device further comprises an actuator. The actuator is coupled to the valve and configured to open the valve to allow flow of conductive fluid through one or more of the lumen of the sheath, the lumen of the needle, or the passageway of the elongate tubular member into the tissue. The actuator is also coupled to the proximal end of the needle, and optionally the sheath, and adapted to cause the distal end of the needle, and optionally the sheath, to extend into the tissue.

Some embodiments of the invention may provide one or more advantages over at least one currently available or previously method, apparatus, and/or system for ablating tissue. In some embodiments, the invention may combine the efficiency and efficacy of "wet" or "virtual" electrode technology with the relative ease of conventional "dry" electrode techniques. By deploying an ablation needle and conductive fluid in a single action, the present disclosure describes at least some methods, systems and apparatuses that may simplify wet electrode tissue ablation procedures. In addition, various embodiments of the invention may simplify dry electrode techniques. For example, by configuring an actuator to be coupled to both a needle and a power source, the needle may be deployed and ablative power may be delivered in a single step. These and other advantages will become evident to one of skill in the art upon reading the disclosure herein.

BRIEF DESCRIPTION OF THE DRAWINGS

FIGS. 11A to 11C are is diagrammatic illustrations of a partially exposed view of a device and a schematic view of a valve according to embodiments of the invention.

Figure 1A:
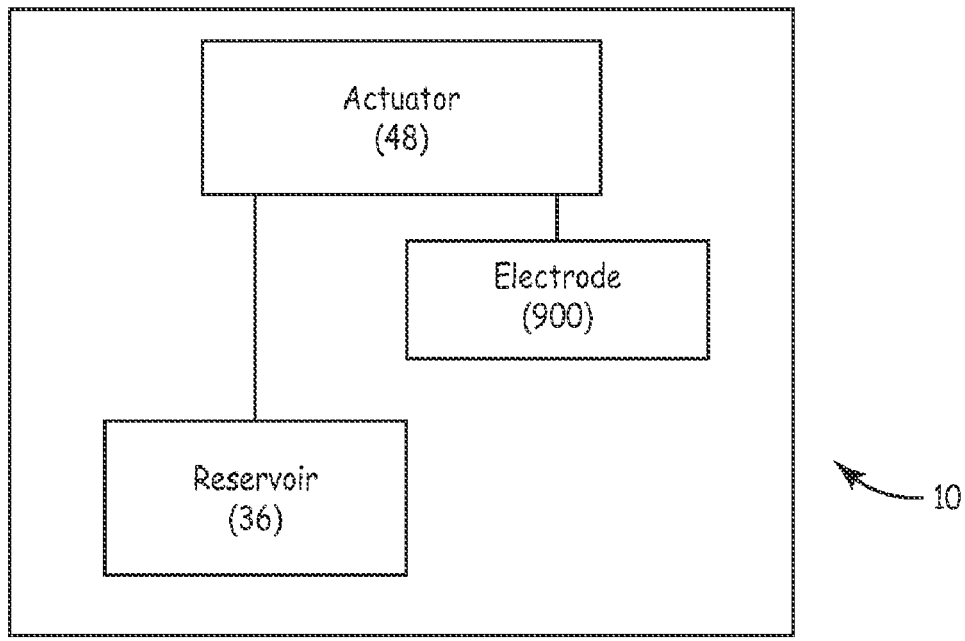
FIGS. 1A and 1B are block diagrams of systems according to embodiments of the invention.

The drawings are not necessarily to scale. Like numbers refer to like parts or steps throughout the drawings. However, it should be understood that use of like reference numbers are for convenience and should not be construed as limiting. For example, the use of the number "10" to refer to "device" in both FIGS. 1 and 4 does not indicate that the device of FIG. 1 must take the form of the device shown in FIG. 4.

TABLE OF REFERENCE NUMBERS

| Term | Reference Number |
|---|---|
| Device | 10 |
| System | 11 |
| Housing | 12 |
| Elongate probe member | 14 |
| Handle | 16 |
| Proximal end of elongate probe member | 18 |
| Distal end of elongate probe member | 20 |
| Passageway | 22 |
| Needle | 24 |
| Needle proximal end | 26 |
| Needle distal end | 28 |
| Sheath | 30 |
| Sheath distal end | 34 |
| Reservoir | 36 |
| Needle lumen | 38 |
| Sheath lumen | 40 |
| Tubing | 42, 42' |
| Discharge member | 44 |
| One-way valve | 46, 46', 46" |
| Actuator | 48 |
| Fluid delivery portion of actuator | 50 |
| Needle delivery portion of actuator | 52 |
| Biasing element | 56 |
| Block | 64 |

-continued

| Term | Reference Number |
|---|---|
| Block guiding member | 66 |
| Block extension | 68 |
| Block extension receiver | 70 |
| Opening of elongate probe member | 72 |
| Fill valve | 74 |
| Fill tubing | 76 |
| Opening | 78 |
| Bladder | 80 |
| Switch | 90 |
| Line | 240 |
| Conductor | 600 |
| Cable | 650 |
| Valve | 890 |
| Valve inlet | 891 |
| Valve outlet | 892 |
| Valve core | 895 |
| Valve bore | 896 |
| Electrode | 900 |
| Energy source | 990 |
| Patient isolation circuit | 1010 |
| Debounce circuit | 1020 |
| Fluid flow controller | 1030 |

DETAILED DESCRIPTION

In the following description, reference is made to the accompanying drawings that form a part hereof, and in which are shown by way of illustration several specific embodiments of the invention. It is to be understood that other embodiments of the invention are contemplated and may be made without departing from the scope or spirit of the present invention. The following detailed description, therefore, is not to be taken in a limiting sense.

The invention, in various embodiments, relates to methods, apparatuses, and systems employing wet electrode technology. In various embodiments, the wet electrode technology may be applied to TUNA procedures, devices and systems. Various patents and patent applications that discuss wet electrode technology and TUNA include:

US 20030073989, Apparatus and method for creating, maintaining, and controlling a virtual electrode used for the ablation of tissue
US 6623515, Straight needle apparatus for creating a virtual electrode used for the ablation of tissue
US 6537272, Apparatus and method for creating, maintaining, and controlling a virtual electrode used for the ablation of tissue
US 6537248, Helical needle apparatus for creating a virtual electrode used for the ablation of tissue
US 20020183733, HELICAL NEEDLE APPARATUS FOR CREATING A VIRUTAL ELECTRODE USED FOR THE ABLATION OF TISSUE
US 20020151884, Apparatus and method for creating, maintaining, and controlling a virtual electrode used for the ablation of tissue
US 6497705, Method and apparatus for creating a virtual electrode used for the ablation of tissue
US 6494902, Method for creating a virtual electrode for the ablation of tissue and for selected protection of tissue during an ablation
US 6409722, Apparatus and method for creating, maintaining, and controlling a virtual electrode used for the ablation of tissue
US 20020058935, METHOD FOR CREATING A VIRTUAL ELECTRODE FOR THE ABLATION OF TISSUE AND FOR SELECTED PROTECTION OF TISSUE DURING AN ABLATION
US 20020058933, Apparatus and method for creating, maintaining, and controlling a virtual electrode used for the ablation of tissue
US 20020049439, Helical needle apparatus for creating a virtual electrode used for the ablation of tissue
US 20020035387, Straight needle apparatus for creating a virtual electrode used for the ablation of tissue
US 20020019628, Method and apparatus for creating a virtual electrode used for the ablation of tissue
US 6315777, Method and apparatus for creating a virtual electrode used for the ablation of tissue
US 6302903, Straight needle apparatus for creating a virtual electrode used for the ablation of tissue
US 20010041921, STRAIGHT NEEDLE APPARATUS FOR CREATING A VIRTUAL ELECTRODE USED FOR THE ABLATION OF TISSUE
US 20010025178, Method and apparatus for creating a bi-polar virtual electrode used for the ablation of tissue
US 6238393, Method and apparatus for creating a bi-polar virtual electrode used for the ablation of tissue
WO 2003047446, FEEDBACK SYSTEM FOR RF ABLATION BY MEANS OF A VIRTUAL ELECTRODE AND COOLING PROTECTION, METHOD THEREFOR
WO 2003005918, APPARATUS AND METHOD FOR CREATING, MAINTAINING, AND CONTROLLING A VIRTUAL ELECTRODE USED FOR THE ABLATION OF TISSUE As those of ordinary skill in the art will readily appreciate upon reading the description herein, at least some of the devices and methods disclosed in the patents and publications cited herein may be modified advantageously in accordance with the teachings of the present invention.

Various embodiments of the invention provide methods and apparatuses for ablating tissue. The methods and apparatuses in some embodiments provide variations of currently available or previously described dry and wet electrode techniques and devices. In at least some embodiments of the invention, methods, devices and systems that are simpler to use than those described to date are provided.

Figure 1B:
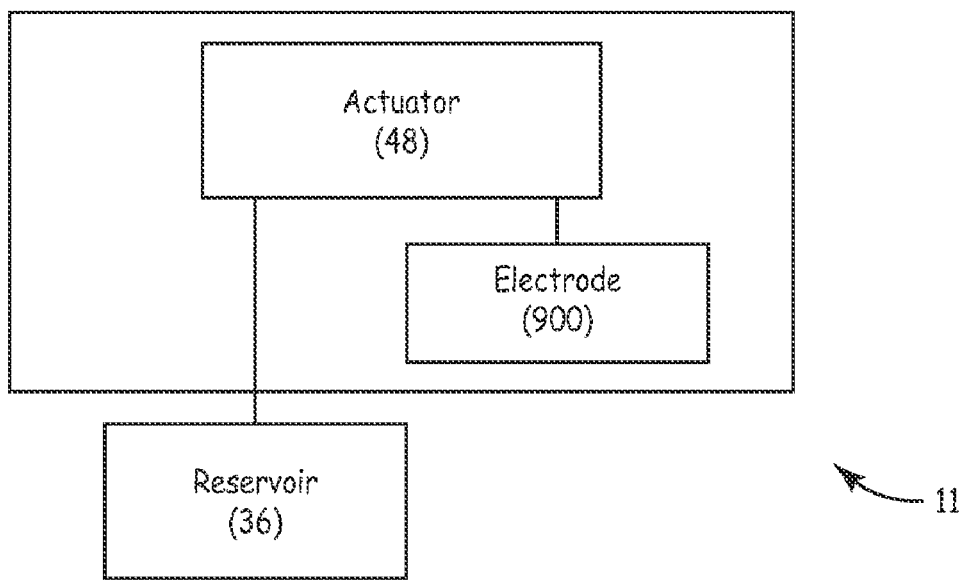

Referring to FIG. 1, an embodiment of the invention provides a tissue ablation device 10 or system 11 comprising an actuator 48 operably coupled to a fluid source reservoir 36 and an electrode 900. The actuator 48 is configured to cause the electrode 900 to enter a target tissue and to cause fluid from the reservoir 36 to flow to the target tissue. The reservoir 36 may be housed in the device 10 (FIG. 1a) or may be external to the device 10 (FIG. 1b).

Reservoir 36 may take the form of any container capable of holding a conductive fluid. Reservoir 36 is preferably made of material compatible with a conductive fluid. Non-limiting examples of materials for forming reservoir 36 include polycarbonate, polyethylene, polypropylene, polyvinyl chloride, ABS, silicone, and polyurethane. Reservoir 36, or a portion thereof, may be rigid or may be compressible. Reservoir 36 may be a part of a pump system (not shown), such as a pump system capable of delivering fluid at a constant rate. When housed within the device 10, it will be understood that the shape and size of reservoir 36 may be modified to accommodate the design of device 10.

Reservoir 36 may be capable of holding any volume of fluid, limited by the design of device 10 or system 11. Preferably reservoir 36 is capable of holding at least enough conductive fluid so that a sufficient amount of conductive fluid may be delivered to a target location during an ablation procedure. It may be desirable for reservoir 36 to be capable of holding at least about 0.1 cc to about 60 cc of fluid, as about 0.1 cc to about 5 cc of conductive fluid will be typically delivered per lesion and about 4 to about 12 lesions may be typically delivered per ablation procedure. Of course, any volume of conductive fluid may be delivered per lesion and any number of lesions may be performed per procedure.

Reservoir 36 may be permanently mounted within device 10, or may be replaceable. Replaceable reservoirs 36 may be suitable for a single tissue ablation procedure or multiple procedures. Preferably, when reservoir 36 is replaceable, reservoir 36 is configured for a single tissue ablation procedure and is prepackaged with sufficient conductive fluid for all of the lesions to be performed in the procedure.

Any electrode 900 suitable for being delivered into a target tissue location and capable of delivering an ablative lesion may be incorporated into a tissue ablation device according to various embodiments of the invention. Electrode 900 is coupled to an electrical energy source (not shown in FIG. 1), such as an RF energy source. Electrode 900 may be coupled to energy source through a conductor. Electrode 900 may be a needle of a tissue ablation device and the needle body may serve as a conductor, or portion thereof.

An embodiment of the invention provides a method for deploying an electrode, such as a needle, and delivering fluid of a tissue ablation device. The method comprises a single step of engaging an actuator 48. The actuator 48 being configured to cause electrode 900 to enter a target tissue location and to cause fluid from a fluid source to flow to the target tissue location. A method for ablating tissue may further comprise applying energy to the target location via the electrode 900 to ablate the tissue. Any device or system capable of deploying an electrode 900 to a target tissue location and delivering fluid to the target tissue location in a single step may be used. For example, the device or system may be a device or system as described in FIG. 1.

Figure 2A:
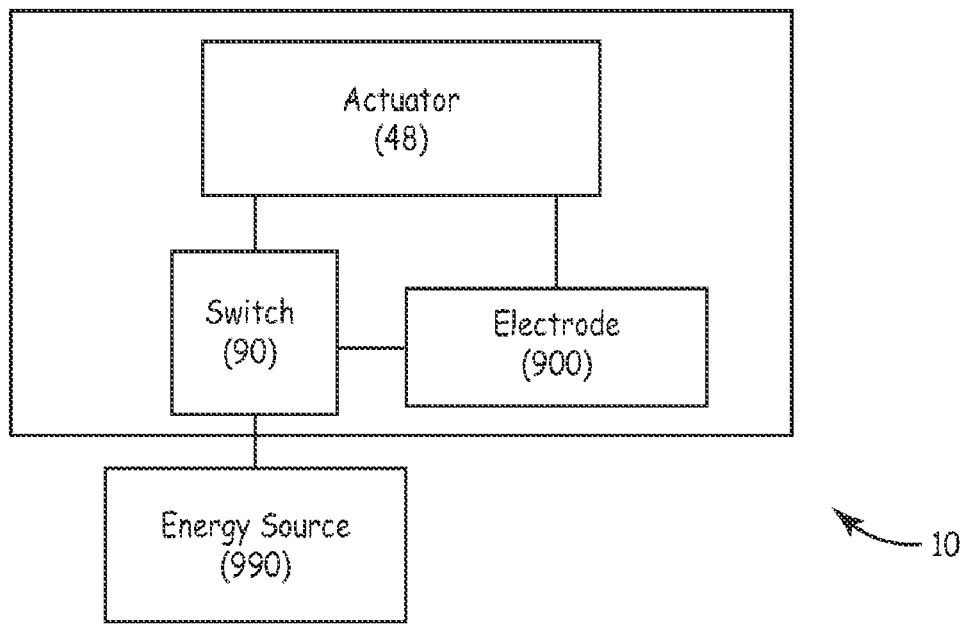
FIGS. 2A and 2B are a block diagram of a system according to an embodiment of the invention.
Figure 2B:
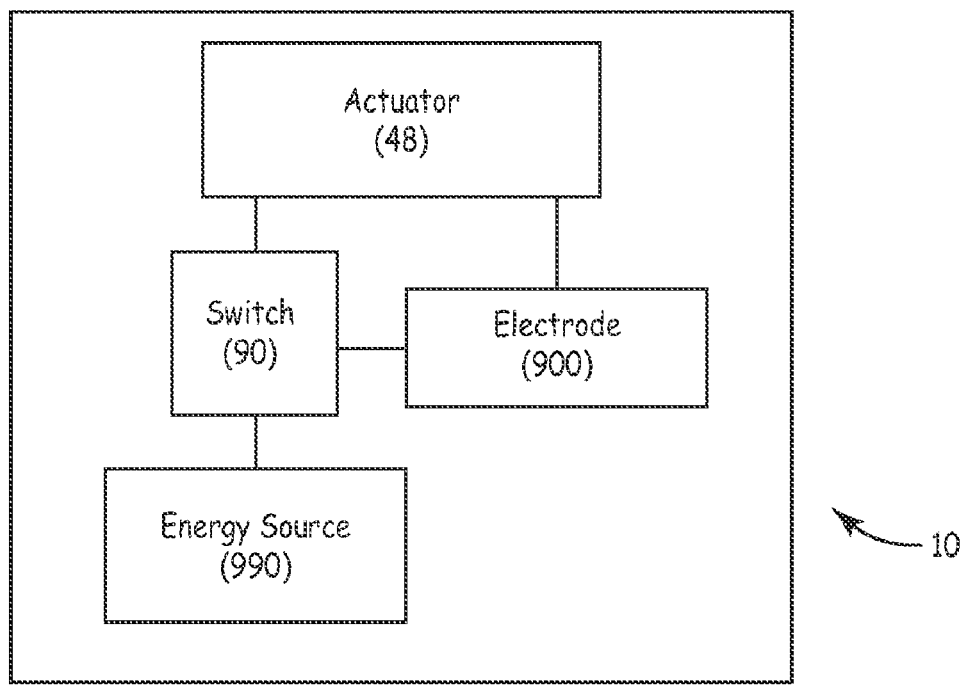

Referring to FIG. 2, an embodiment of the invention provides a tissue ablation device comprising an actuator 48 operably coupled to an electrode 900 and an energy source 990. Energy source 990, such as an RF generator, may be within device 10 or external to device 10. The actuator 48 is configured to cause the electrode 900 to enter a target tissue and to cause energy to flow from the energy source 990 to the electrode 900. Actuator 48 may be coupled energy source 990 through a switch 90, which can allow or prevent energy flow from energy source 990 to electrode 900. For example, actuator 48 may be configured to cause switch 90 to close or complete an electrical circuit, thereby allowing energy to flow from energy source 990 to electrode, when actuator 48 is engaged. Also by way of example, actuator 48 may be configured to cause switch 90 to open or disconnect an electrical circuit, thereby preventing energy to flow from energy source 990 to electrode, when actuator 480 is disengaged. Alternatively, actuator 48 may be configured to prevent switch 90 from closing the circuit, as opposed to causing switch 90 to open the circuit, when actuator 48 is disengaged. The actuator may also be coupled to a fluid source reservoir 36, and be configured to and to cause fluid from the reservoir 36 to flow to the target tissue, as shown in FIGS. 3A-3F, in a substantially similar manner as with the embodiment of FIG. 1.

Figure 3A:
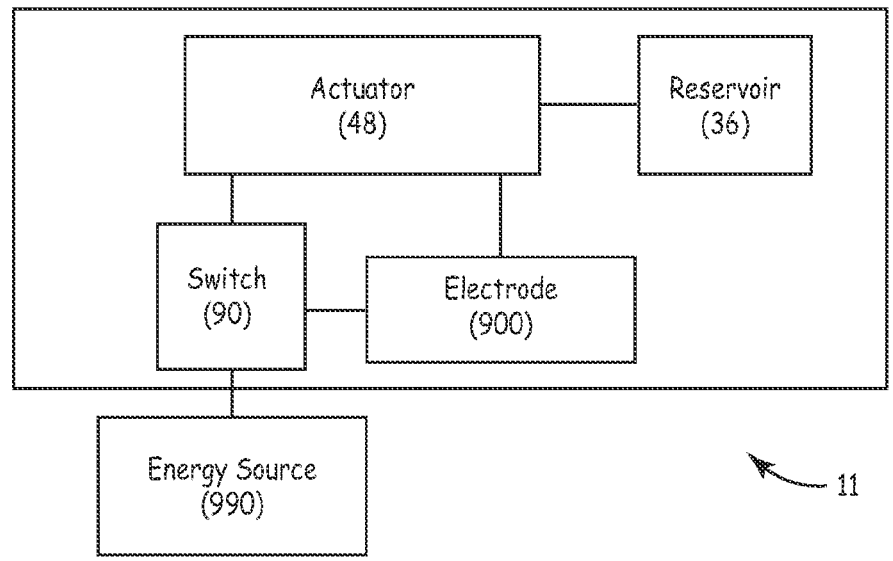
FIGS. 3A to 3H are block diagrams of systems according to embodiments of the invention.
Figure 3B:
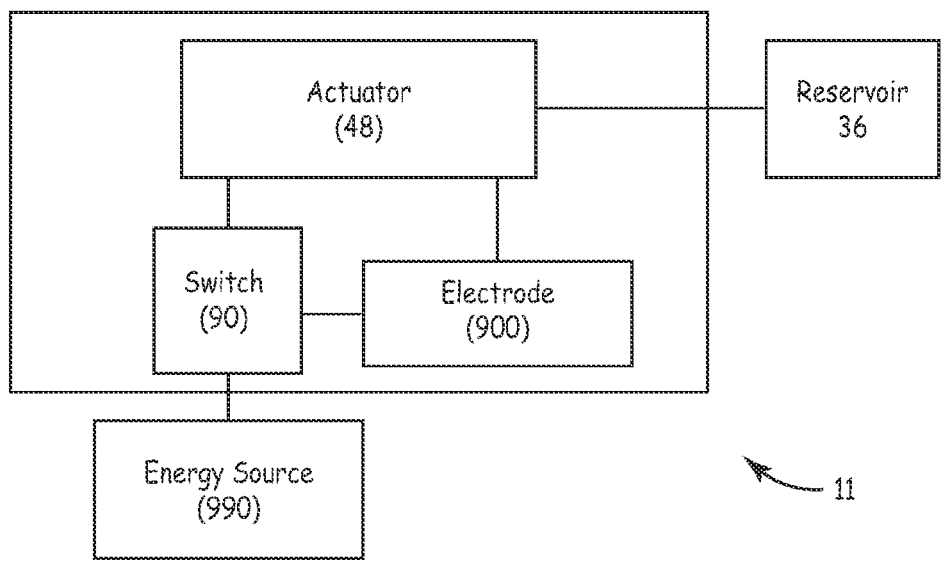
Figure 3C:
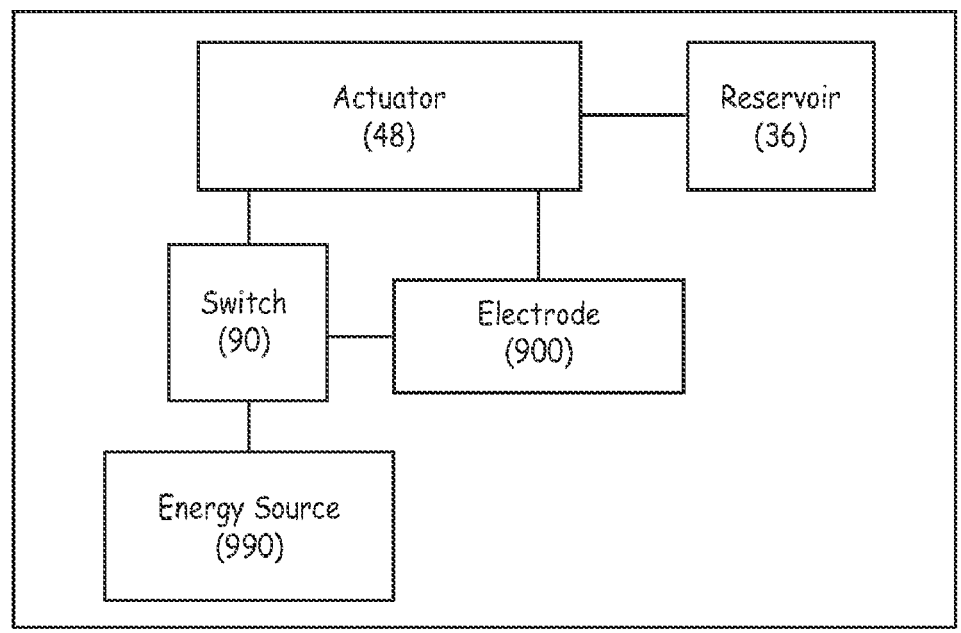
Figure 3D:
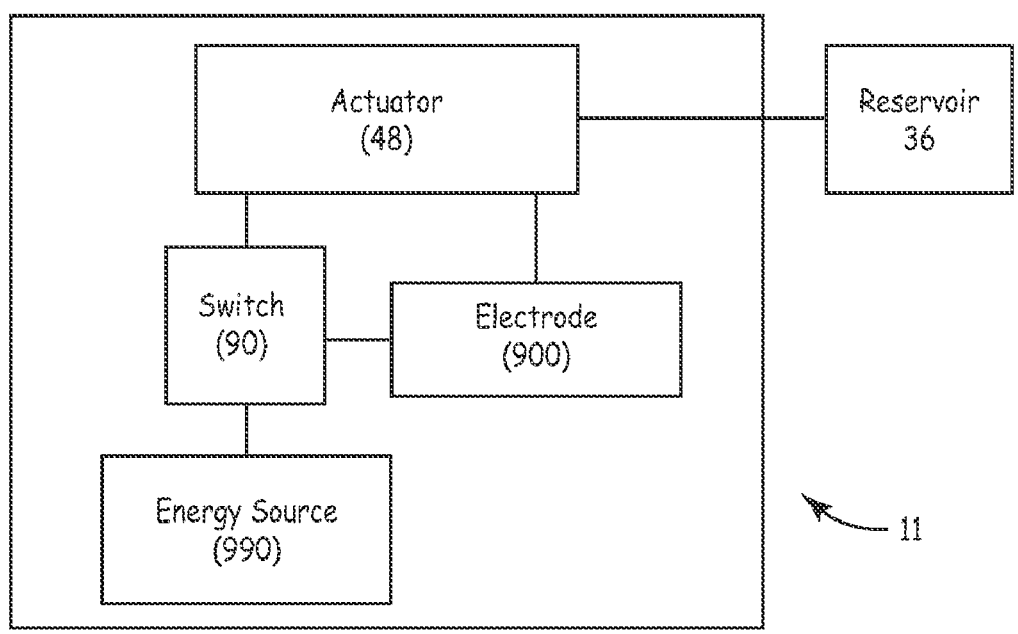
Figure 3E:
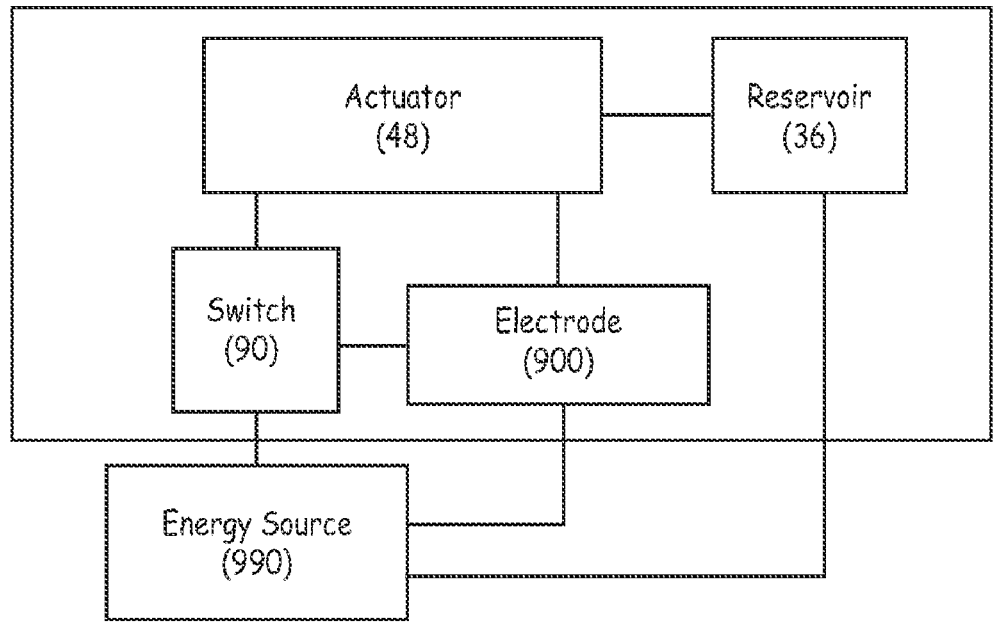
Figure 3F:
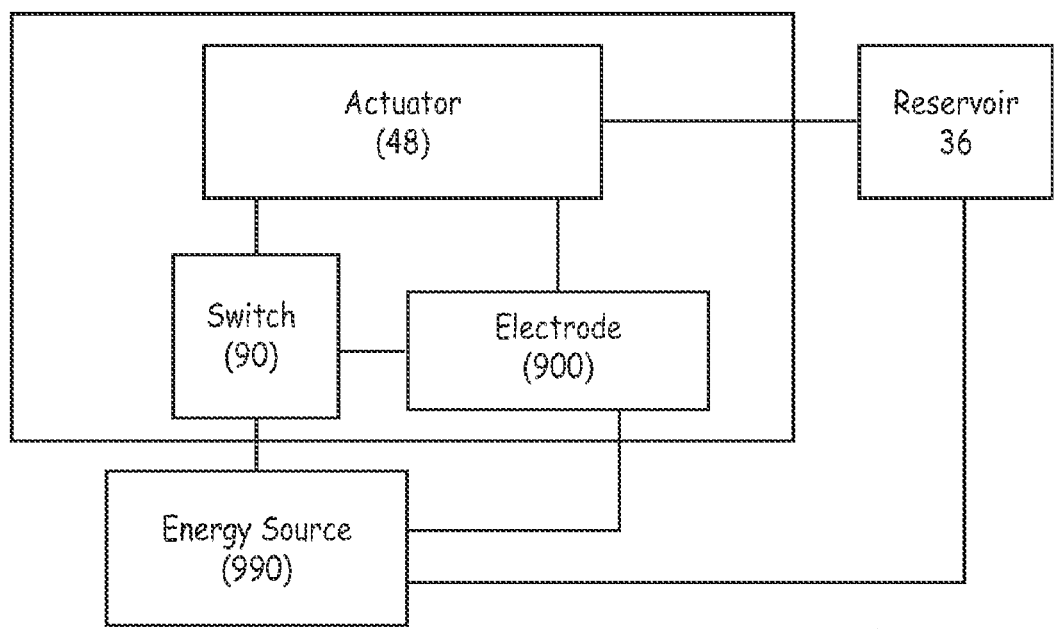
Figure 3G:
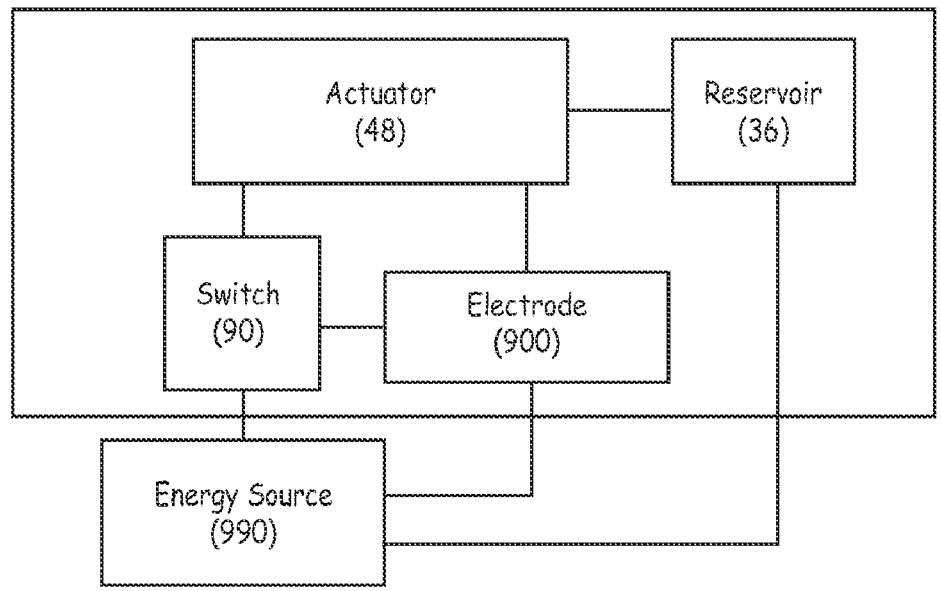
Figure 3H:
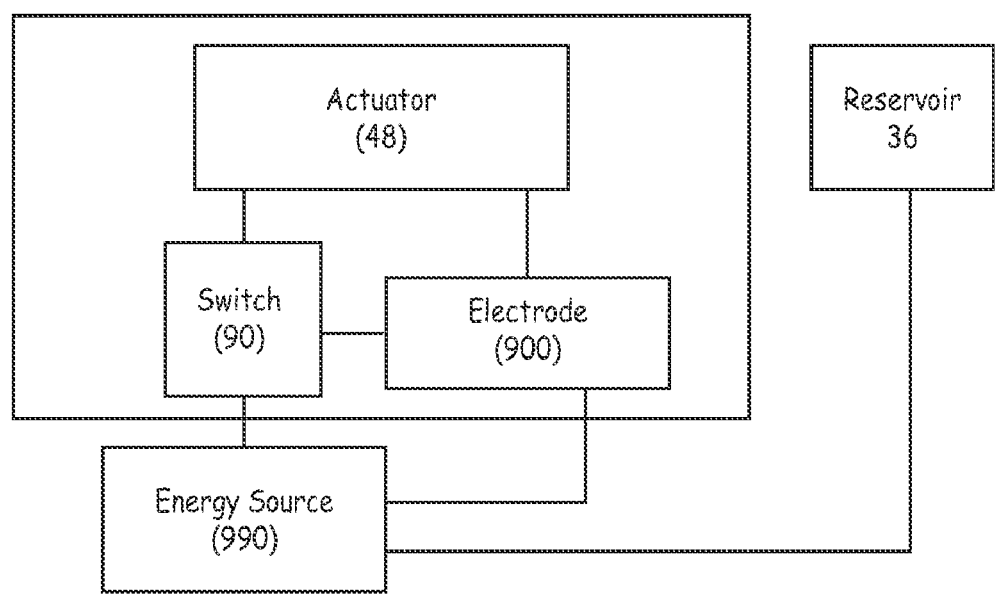

FIGS. 3E-3H show embodiments where energy source 990 is coupled to reservoir 36. In such embodiments reservoir 36 may be coupled to energy source 990 through e.g., a pump system (not shown). The pump system may comprise the reservoir 36 and energy source 990 may provide energy to the pump system such that fluid may be pumped from reservoir 36 to the target tissue. In FIGS. 3G and 3H, actuator 48 is not coupled to reservoir 36. In such embodiments, engaging actuator 48 activates switch 90 to complete circuit, allowing energy to flow from energy source 990 to electrode 900 and to reservoir 36, which may be a part of a pump system. In FIGS. 3E and 3F, both actuator 48 and energy source 990 are coupled to reservoir 36.

Alternative coupling, whether direct or indirect, between actuator 48, energy source 990, reservoir 36, and/or electrode 900, are also contemplated. Alternative configurations are also contemplated.

Figure 13A:
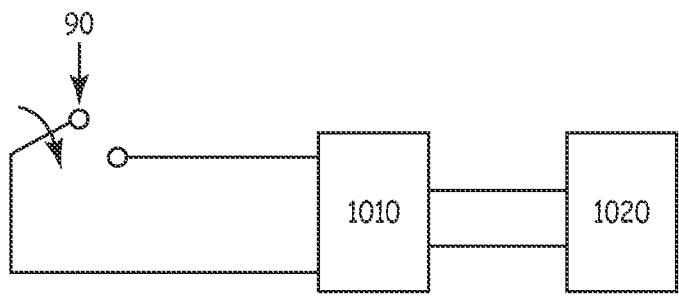
FIGS. 13A and 13B are is block diagram of a circuit according to an embodiment of the invention.
Figure 13B:
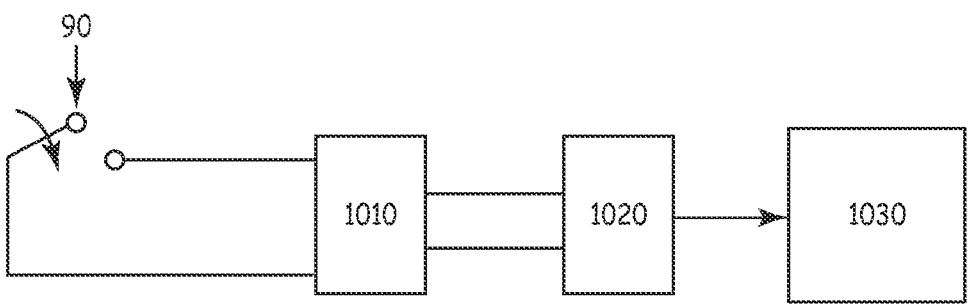

Referring to FIG. 13, an exemplary diagram showing a circuit between switch 90 and energy source 990 is shown. Switch 90 is activated to complete the circuit. Any suitable switch mechanism may be used. For example, the switch mechanism may be a momentary push button switch. The circuit may comprise a patient isolation circuit 1010 to isolate the patient electrically from unsafe voltages. The circuit may comprise a debounce circuit to filter double switch "pushes", switch "chatter", and the like. As shown in FIG. 13B, the circuit may comprise a controller of fluid flow 1030. The controller 1030 may be hardware or software. The controller 1030 may be integrated into the circuit by a switch, such as e.g. push on switch, a push off switch, push and hold on switch, release off switch, and the like.

As used herein, "single step" means a single action and may be an action comprising separate parts. For example, the single step may be engaging an actuator 48. The separate parts may be (a) partially engaging the actuator 48 to a first position and then completely engaging the actuator 48 from the partially engaged state, (b) partially engaging the actuator 48 to a first position, further engaging the actuator 48 the a second position, and further engaging the actuator 48 to a third position, and (c) the like. In an embodiment, when the engaged to a first position or during engagement to the first position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode. In an embodiment, when engaged to a second position or during engagement to the second position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode. In an embodiment, when the engaged to a third position or during engagement to the third position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode.

The methods and apparatuses of various embodiments of the invention may be used to treat a disease or disorder in a mammal, such as a human patient. Such apparatuses may be part of a system 11 and may be in the form of a transurethral needle ablation apparatus or device 10 similar to the apparatus shown in U.S. Pat. No. 5,964,756 and in U.S. patent application Ser. No. 09/684,376 filed Oct. 5, 2000, the entire content of each of which is incorporated herein by this reference. An exemplary device 10 and system 11 that may be modified according the teachings of the present invention is Medtronic's Precision™ Plus TUNA System. The Precision™ Plus TUNA System, devices, and components thereof, as well as associated Medtronic brochures and user guides, are hereby incorporated herein by reference, each in its respective entirety.

Figure 4:
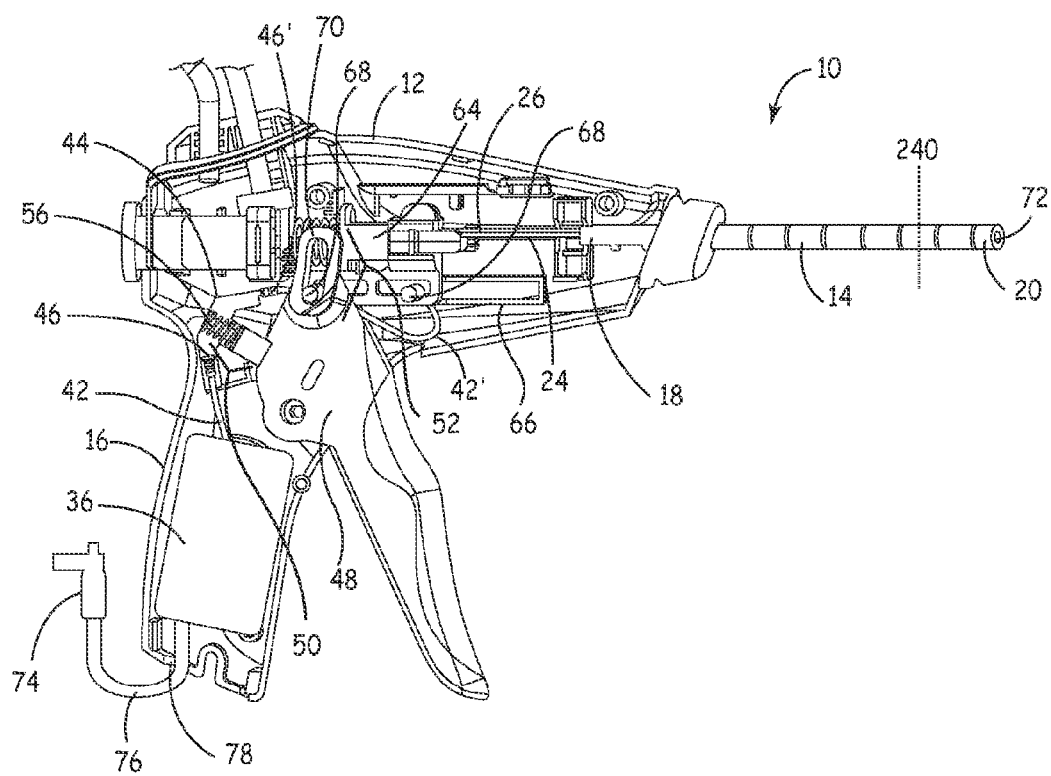
FIG. 4 is a diagrammatic illustration of a view of a partially exposed view of a device according to an embodiment of the invention.

An embodiment of the invention provides a device 10 for ablating tissue. As shown in FIG. 4, the device 10 comprises a housing 12 and an elongate probe member 14 extending from the housing 12. The housing may comprise a handle 16 extending from the housing 12. The elongate probe member comprises a proximal end 18 and a distal end 20, and one or more passageways 22 (see, e.g. FIG. 7) extending at least substantially between the proximal end 18 of the elongate probe member 14 to the distal end 20 of the elongate probe member 14. The device 10 further comprises one or more needles 24.

Figure 7:
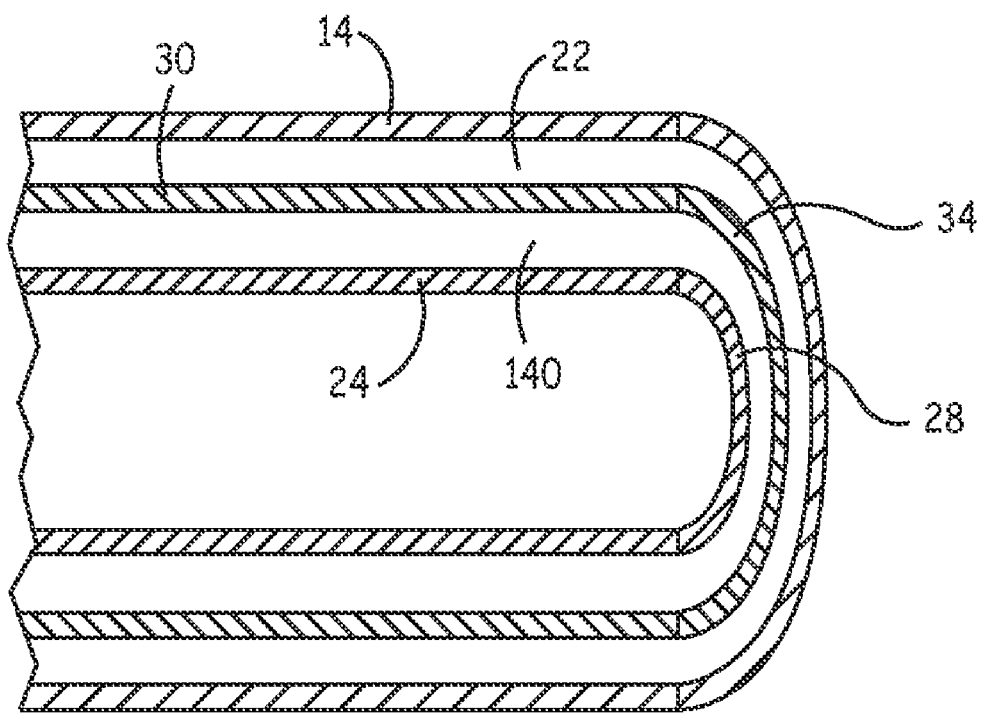
FIG. 7 is a diagrammatic illustration of a longitudinal section of a portion of a device as in FIG. 4.

As shown in FIG. 7, the one or more needles 24 may be slidably mounted within one of the one or more passageways 22 of the elongate probe member 14. The needle 24 may comprise a lumen 38 extending at least substantially between a needle proximal end 26 and a needle distal end 28. The device 10 may further comprise one or more sheaths 30 (not shown in FIG. 4). A sheath 30 has a proximal end and a distal end 34, and a lumen 40 extending at least substantially between the sheath proximal end and the sheath distal end 34. The sheath(s) 30 is slidably mounted within the one or more passageways 22 of the elongate probe member 14. When the device 10 comprises a sheath 28, a needle 24 may be slidably disposed within the lumen 40 of sheath 28. The sheath may be an insulative sheath 28.

Referring to FIG. 4, the device 10 further comprises a reservoir 36. The reservoir 36 is operably coupled to, and in fluid communication with, one or more lumens 38 of one or more needles 24, one or more lumens 40 of one or more sheaths 30, and/or one or more passageways 22 of elongate probe member 14. The reservoir 36 may be coupled to the passageway(s) 22 or lumens 38/40 via tubing 42. Any suitable tubing material, such as PVC, silicone, or polyurethane, may form tubing 42. As shown in FIG. 4, tubing 42 may be inserted into reservoir 36 and extend to discharge member 44. Discharge member 44 may be formed of any suitable material. By way of example, discharge member 44 may be formed of polycarbonate, polyethylene, polypropylene, or ABS. A one-way valve 46 may be coupled to tubing 42 to allow flow of conductive fluid from the reservoir 36 to the discharge member 44 and to prevent flow of fluid from the discharge member 44 to the reservoir 36. One-way valve 46 may be made be, e.g., a silicone valve, a Teflon valve, or a polyurethane valve. The one-way valve 46 in FIG. 4 is shown in proximity to discharge member 44, but it will be understood that one-way valve 46 may be coupled to tubing 42 at any location between reservoir 36 and discharge member 44. Tubing 42' may be used to couple discharge member 44 to needle lumen(s) 38, sheath lumen(s) 40 and/or passageway(s) 22 (only connection to needle 24 shown in FIG. 6).

A fill valve 74 may be connected to the reservoir 36 to fill or refill reservoir 36 with fluid. As shown in FIG. 4, fill valve 74 may be connected to reservoir through fill tubing 76. A supply of fluid (not shown) may be connected to fill valve 74. The supply of fluid may be under constant pressure, such that opening the valve, allows fluid to flow into reservoir 36. Fill valve 74 may comprise a stopcock or other suitable means, and the stopcock or other suitable means may be turned or engaged to allow fluid to flow into reservoir 36. Fill tubing 76 may extend from handle 16, through an opening 78 in handle 16 to allow external access to fill valve 74. Of course fill valve 76 may be placed anywhere with respect to housing 12. For example, fill valve 76 may be attached to handle 16. Fill valve 74 may also be directly coupled to reservoir 36, such that fill tubing 76 is omitted from device 10. Of course, any suitable means for filling or refilling reservoir 36 and for reservoir 36 access may be used. For example, an access port (not shown) may be used. Access port may comprise a septum, through which a needle may be inserted. Access port may be directly coupled to reservoir 36 or may be coupled to fill tubing 76, which is coupled to reservoir 36.

An O-ring or other suitable seal may be used to create a fluid-tight seal between tubing 22 and reservoir 36, tubing 22, 22' and discharge member 44, fill tubing 76 and reservoir 36, etc.

Figure 6:
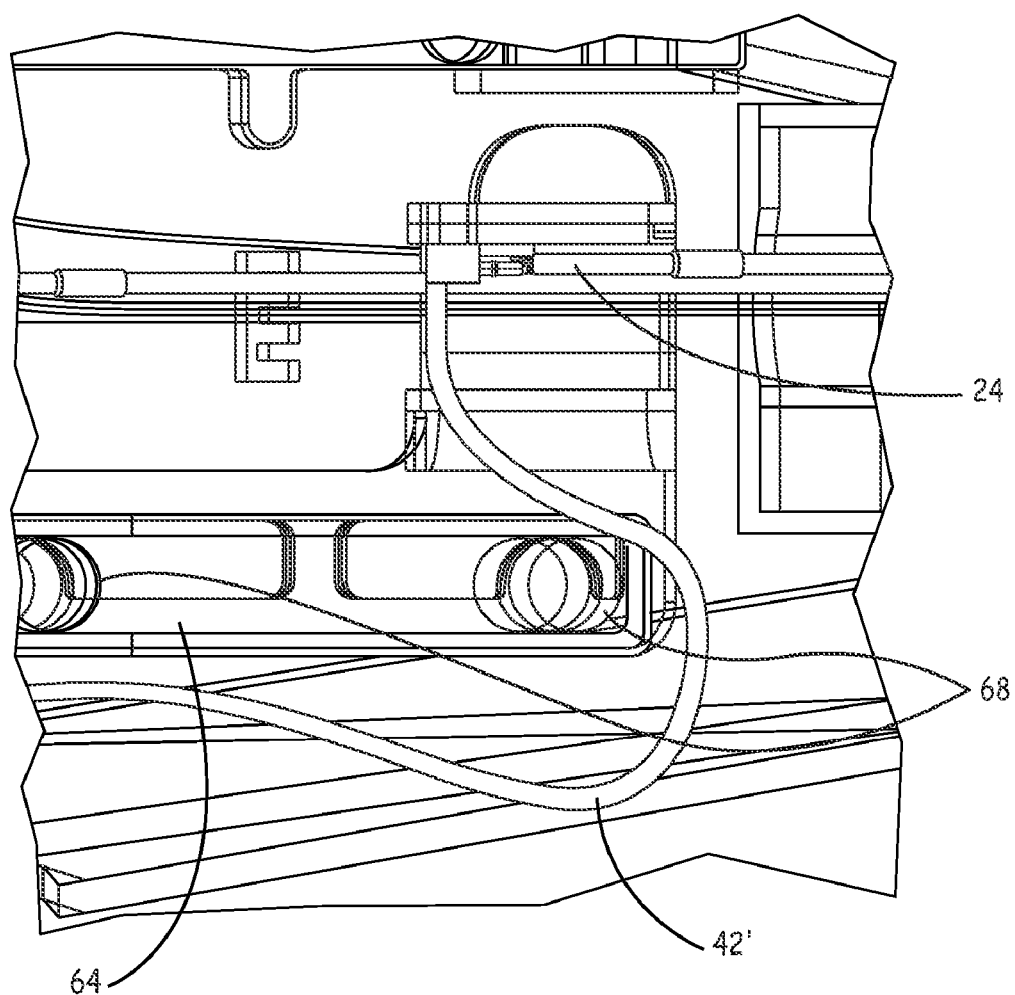
FIG. 6 is a diagrammatic illustration of an exploded view of a portion of a partially exposed device as in FIG. 4.

As shown in FIG. 6, tubing 42' is coupled to needle 24 such that a lumen of the tubing is in fluid communication with a lumen 38 of needle 24. While not shown, it will be understood that similar connections may be made such that a lumen of tubing 42' may be in fluid communication with a sheath lumen 40 and/or passageway 22. It will be further understood that tubing 42' may comprise multiple lumens through which the tubing may be placed in fluid communication with one or more needle lumens 38, one or more sheath lumens 40, and/or one or more passageways 22. The multiple lumens may be concentric, side-by-side, etc. A Y-connector (not shown) may be used to couple tubing 42' to more than one, e.g., needle 24. Alternatively, a plurality of tubing 42' may be run from discharge member 44 to a plurality of needles 24. A one-way valve 46' may be coupled to tubing 42' to allow fluid to flow from discharge member 44 to needle lumen 38, sheath lumen 40, and/or passageway 22, and to prevent flow from needle lumen 38, sheath lumen 40, and/or passageway 22 to discharge member 44. The one-way valve 46' in FIG. 6 is shown in proximity to discharge member 44, but it will be understood that one-way valve 46' may be coupled to tubing 42' at any location between discharge member 44 and needle lumen 38, sheath lumen 40, and/or passageway 22.

The device further comprises an actuator 48 extending from the housing 16. The actuator 48 comprises a fluid delivery portion 50 and a needle delivery portion 52. The fluid delivery portion 44 is operably coupled to the reservoir 36 and adapted to cause fluid to flow from the reservoir to needle lumen 38, sheath lumen 40, and/or passageway 22 and into body tissue. As shown in FIG. 4, the fluid delivery portion 50 of actuator 48 is coupled to discharge member 44. A fluid tight seal is formed between discharge member 44 and fluid delivery portion 50 of actuator. A biasing element 56, in the form of a spring coil in FIG. 4, is disposed within discharge member 44. A first end portion of biasing element 56 is configured to engage an internal surface of discharge member 44. A second end portion of biasing element 56 is configured to engage fluid delivery portion 50 of actuator 48. Biasing element 56 facilitates return of actuator 48 to a disengaged position after the actuator 48 is engaged. Of course, biasing element 56 may be placed in any location within device 10 to accomplish the return of the actuator 48 to a disengaged position. Alternatively, biasing element 56 may not be present in device 10.

Fluid delivery portion 50 of actuator 48, in combination with reservoir 36 and discharge member 44, may utilize squirt gun type technology to draw fluid from reservoir 36 and deliver the fluid to needle lumen 38, sheath lumen 40, and/or passageway 22. It will be understood that the device 10 may be primed, by for example engaging and disengaging the actuator 48, prior to using the device. Priming allows fluid to be loaded in fluid path between reservoir 36 and one or more needle lumens 38, one or more sheath lumen 40, and/or one or more passageway 22 of elongate probe member 14, such that a subsequent engagement of actuator 48 will cause the fluid to flow into a target tissue area. In the embodiment depicted in FIG. 4, a portion of fluid delivery portion 50 of actuator 48 is disposed within biasing element 56 coil. Engaging the actuator 48 inserts at least a portion of fluid delivery portion 50 into discharge member 44, increasing pressure in the discharge member 44 relative to lumen of tubing 42' and forcing fluid from discharge member to lumen of tubing 42' and one or more needle lumens 38, one or more sheath lumens 40, and/or one or more passageways 22 of elongate probe member 14. Disengaging the actuator 48 withdraws at least a portion of fluid delivery portion 50 from discharge member 44, creating a pressure drop in discharge member 44 relative to reservoir 36 causing fluid to move from reservoir 36 to discharge member 44 through tubing 42. The one-way valves 46, 46' ensure that fluid moves in the desired flow path.

Of course fluid delivery portion 50 of actuator 48 may be coupled to reservoir 36 in any manner suitable to deliver fluid from reservoir 36 to needle lumen 38, sheath lumen 40, and/or passageway 22 when actuator 48 is engaged. For example, fluid delivery portion 50 of actuator 48 may increase pressure in reservoir 36, when actuator 48 is engaged, to force fluid to flow from reservoir 36 through tubing 22, 22' to needle lumen 38, sheath lumen 40, and/or passageway 22. By way of further example, fluid delivery portion 50 of actuator 48 may compress reservoir 36 or a fluid containing portion thereof when the actuator is engaged. Alternatively, reservoir 36, or fluid containing portion thereof, may be placed under pressure by a reservoir biasing element (not shown) or pump (not shown) and fluid delivery portion 50 of actuator 48 may be operatively coupled to a valve that allows pressurized fluid to flow from reservoir 36 to tubing 22, 22', needle lumen 38, sheath lumen 40, and/or passageway 22 when actuator 48 is engaged but prevents flow when actuator 48 is disengaged (see, e.g. FIG. 11). Similarly, fluid may be supplied from an external source (not shown) under, e.g. constant pressure, and reservoir 36 may be omitted. In such embodiments, discharge member 44, may be omitted from the device.

Referring to FIG. 9, an embodiment of the invention where fluid delivery portion 50 of actuator 50 is coupled to reservoir in a syringe-like fashion is shown. Reservoir 36 is fluidly coupled to discharge member 44 through tubing 42. A one-way valve 46 is disposed in tubing 42 between reservoir 36 and discharge member 44. One-way valve 46 allows fluid to flow from reservoir 36 to discharge member 44, but prevents fluid from flowing from discharge member 44 to reservoir 36. Fluid delivery portion 50 of actuator 48 is slidably disposed within discharge member 44. Preferably, fluid delivery portion 50 is disposed in discharge member 44 in a fluid tight manner. A fluid delivery portion 50, or a portion thereof, may have an outer diameter substantially similar to an inner diameter of a portion of discharge member 44 through which fluid delivery portion 50 of actuator 48 slides. Discharge member 44 is fluidly coupled to a lumen, e.g. needle lumen 38, sheath lumen 40, and/or passageway 22, via tubing 42'. A one-way valve 46' may be disposed between in tubing 42' between reservoir 36 and lumen (e.g., 38, 40, 22). One-way valve 46' allows fluid to flow from reservoir 36 to lumen (e.g., 38, 40, 22) but prevents flow from lumen (e.g., 38, 40, 22) to reservoir 36.

Figure 9A:
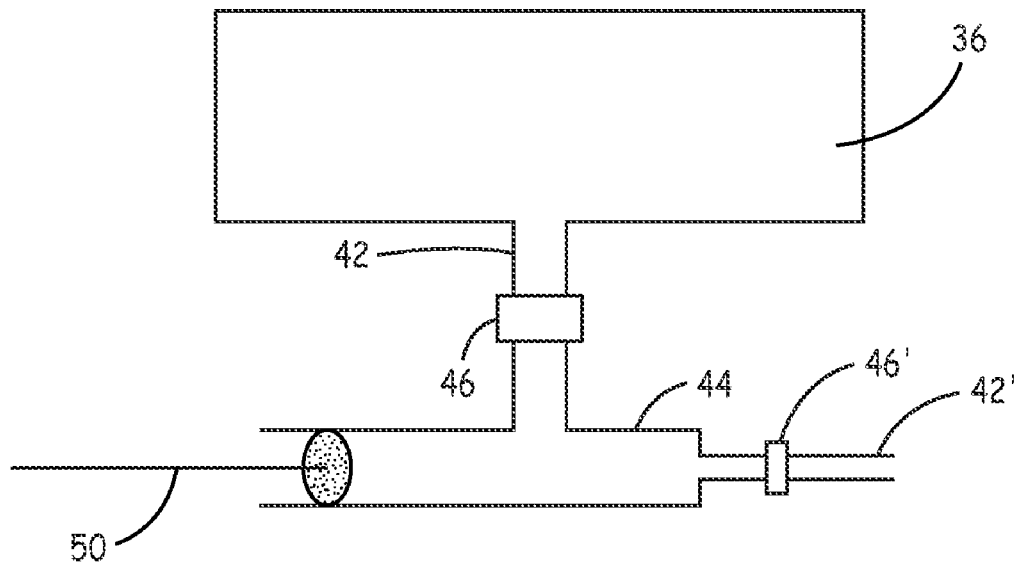
FIGS. 9A and 9B are a diagrammatic illustration of a perspective view of a portion of a device according to an embodiment of the invention.
Figure 9B:
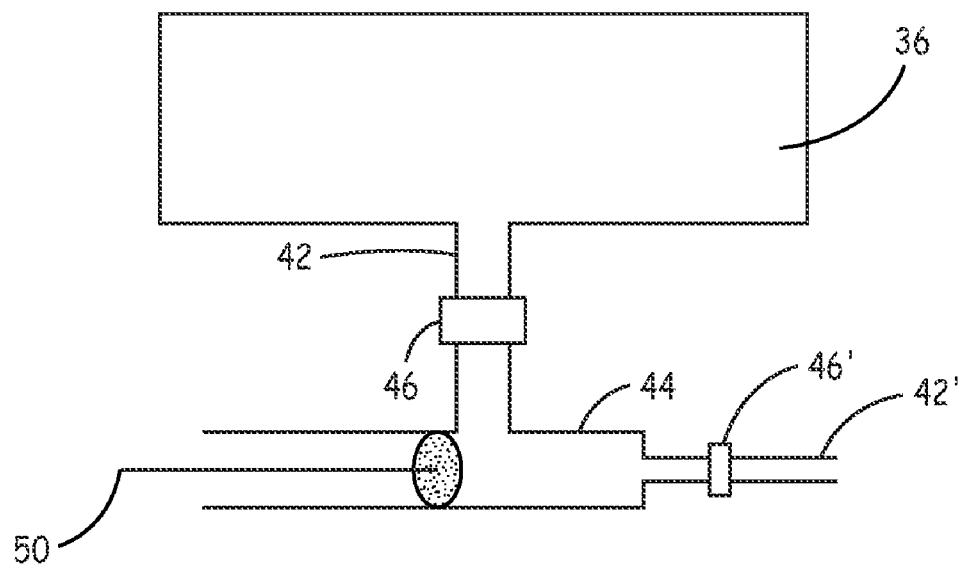

In FIG. 9a, actuator 48 is engaged. The process of engaging the actuator 48 causes fluid delivery portion 50 of actuator 48 to slide through discharge member 44 to cause fluid in discharge member 44 to be discharged through tubing 42' to lumen (e.g., 38, 40, 22). In FIG. 9b, the actuator 48 is disengaged. The process of disengaging the actuator 48 causes the fluid delivery portion 50 of the actuator 48 to slide through discharge member 44, reducing pressure in discharge member 44 relative to reservoir 36 such that fluid flows from reservoir 36 into discharge member 44. Accordingly, fluid for a subsequent lesion will be present in discharge member 44 and prepared for discharge upon subsequent engagement of actuator 48. It should also be understood that, depending on the configuration of reservoir 36 and discharge member 44 within device 10, gravity may assist in causing fluid to flow from reservoir 36 to discharge member 44 when actuator 48 is disengaged or in the process of being disengaged.

Figure 10A:
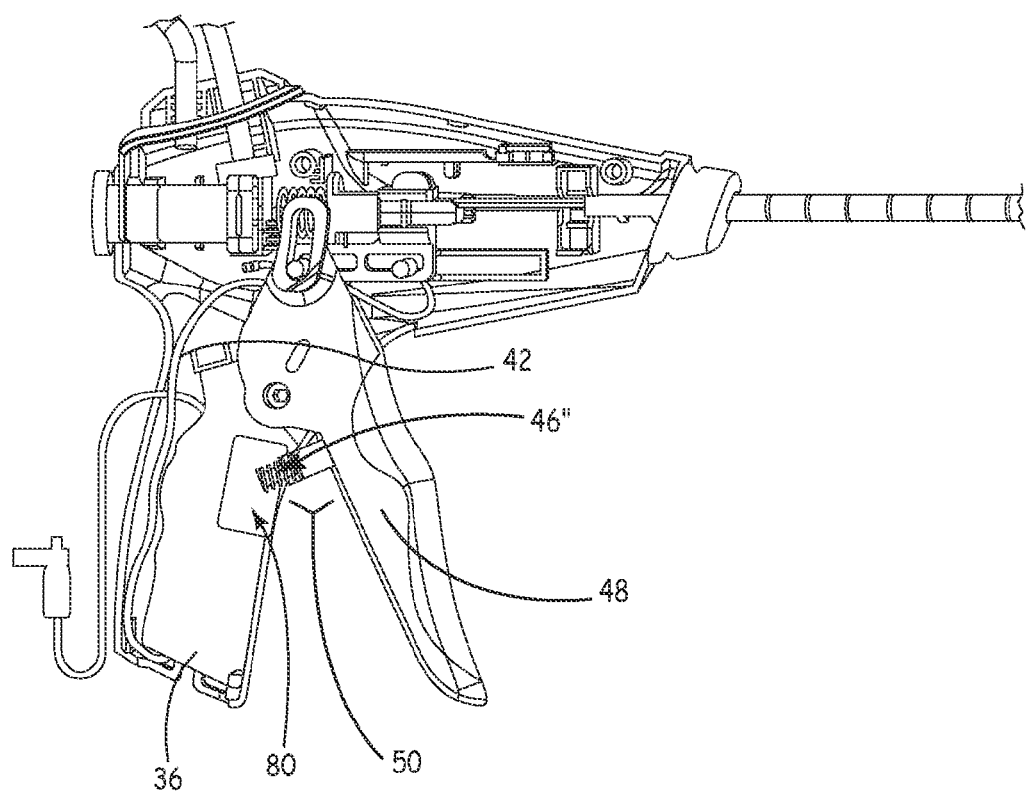
FIGS. 10A and 10B are a diagrammatic illustration of a partially exposed view of a device according to an embodiment of the invention.
Figure 10B:
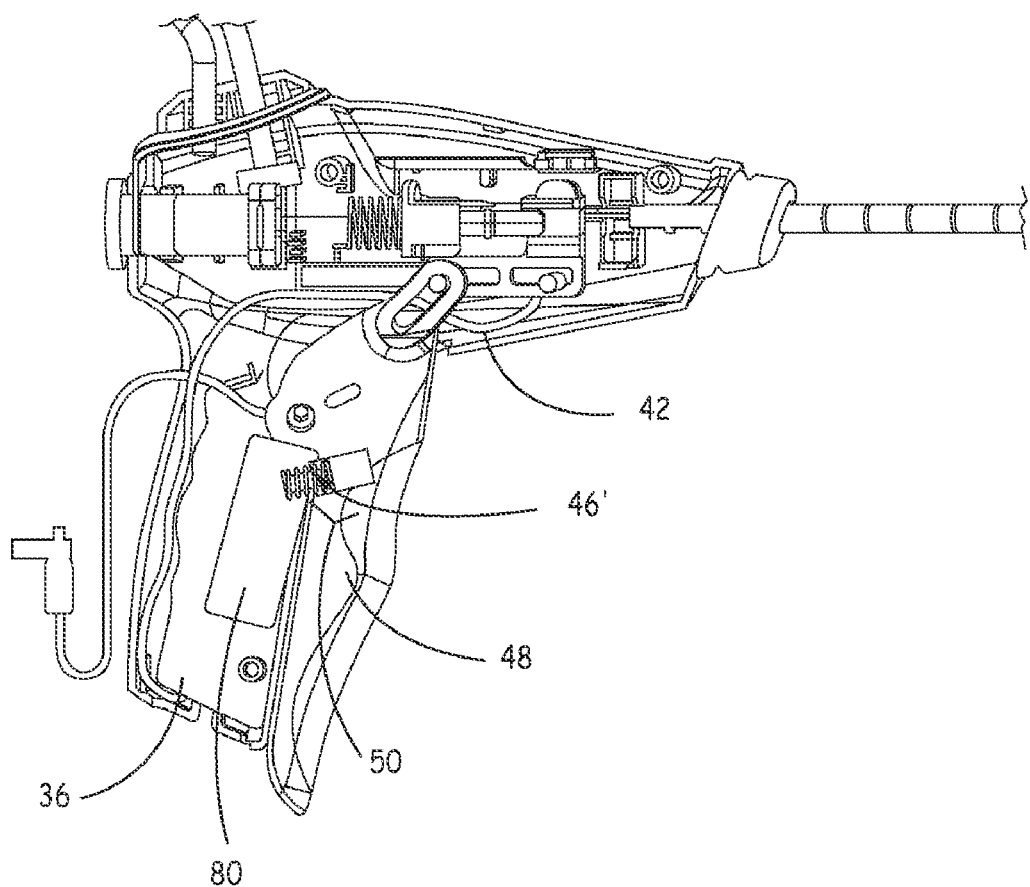

In an embodiment, the reservoir 36 may comprise an expandable bladder 80 that pressurizes fluid to be delivered from device 10. In the embodiment shown in FIG. 10, bladder 80 is disposed within reservoir 36. Bladder 80 is in fluid communication with external environment of device 10 through one-way valve 46". One way valve 46" allows air to flow from outside bladder 80 into bladder 80, but prevents flow of air from inside bladder 80 to outside bladder 80. Fluid delivery portion 50 of actuator 48 is coupled to bladder 80, such that the process of engaging actuator 48 (actuator shown engaged in FIG. 10b an disengaged in FIG. 10a) forces air into expandable bladder 80 causing bladder to expand. As bladder 80 expands, fluid is forced from reservoir 36 through tubing 42 through lumen (e.g., 38, 40, 22).

Alternatively and as shown in FIG. 11a, actuator 48 may be coupled to valve 890 disposed in tubing 42, bladder 80 may be expanded, and fluid in reservoir 36 may be pressurized prior to engaging actuator 48, such that engaging actuator 48 opens valve 890 to allow fluid to flow through valve 890. Reservoir 36 may come pre-packaged with an expanded bladder 80 and pressurized fluid. Alternatively, bladder 80 may be expanded prior to use through a separate trigger, pump, etc. mechanism (not shown). In the embodiment depicted in FIG. 11, tubing 42 may be connected to inlet 891 and outlet 892 of valve 890. Valve 890 in FIG. 11 includes a valve core 895 with a bore 896. In FIG. 11c, the valve core 895 is positioned such that fluid moving into the valve 890 through the inlet 891 can flow to the outlet 892 after passing through the bore 896, and corresponds to actuator 48 being engaged. In FIG. 11b, valve 890 is in a closed position such that fluid may not flow through valve 890, corresponding to actuator 46 being disengaged. Sealing between the valve core 895 and the valve body may be by any suitable technique. In some instances, close tolerances in the valve 890 and the viscosity of the fluids being used may be sufficient. In other instances, it may be desirable to use grease, o-rings, gaskets, etc. to provide sealing that prevents or reduces unwanted flow through the valve 890. The valve 890 shown in FIG. 11 is a linear valve in which transitional movement of valve core 895 by actuator 46 changes the valve between an open position (FIG. 11c), in which actuator is engaged, and a closed position (FIG. 11b), in which actuator is disengaged. However, it will be understood that any suitable valve 890 may be used. Further, it will be understood that a reservoir 36 may not be present in a device 10 where actuator 48 is coupled to a valve 890, and that fluid may be supplied from a source outside of device 10, such as, e.g., an external pump (not shown), as shown in e.g. FIG. 12.

Figure 12A:
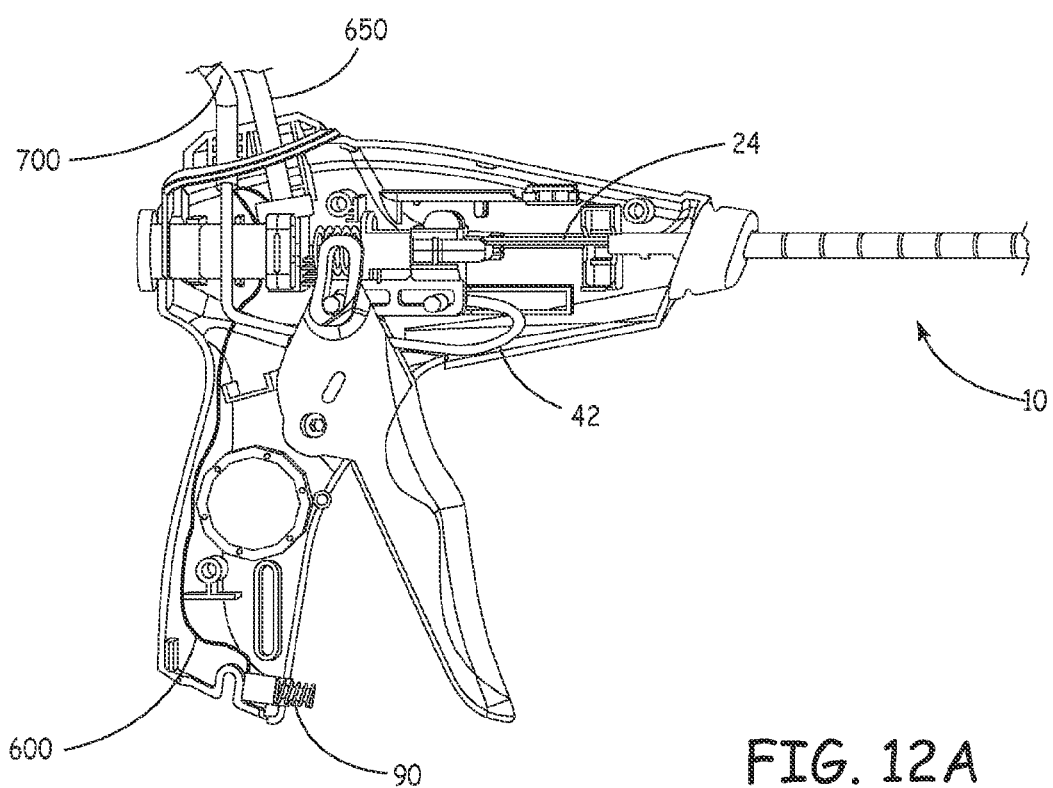
FIGS. 12A and 12B are a diagrammatic illustration of a partially exposed view of a device according to an embodiment of the invention.
Figure 12B:
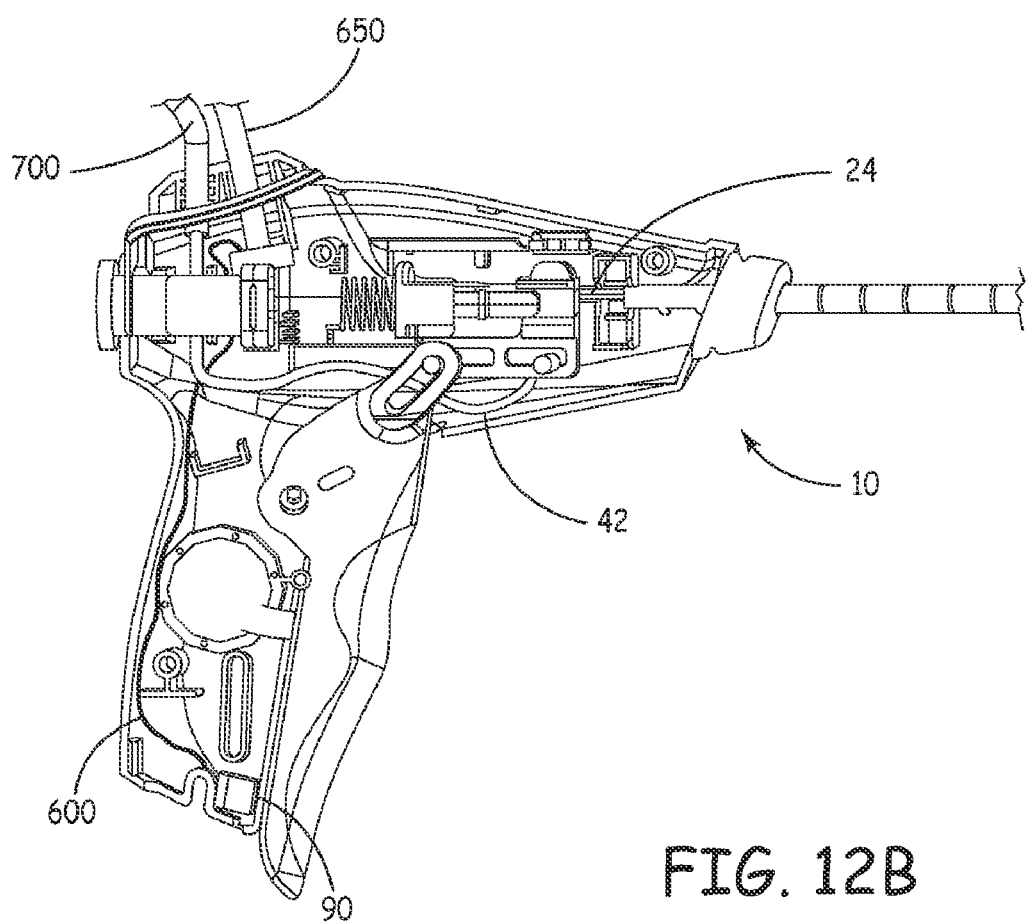

FIG. 12 shows a device 10 comprising a switch 90, such as an electrical contact. Switch 90 is operably coupled to conductor 600, such as a cable or wire. Conductor 600 is shown as being coupled to cable 650, which is operably coupled to an energy source 990 (not shown) external to device. Cable 650 may also be operably coupled to a pump (not shown) containing a reservoir 36, which may be external to device 10. Engaging actuator 48 activates switch 90, e.g. depresses electrical contact, to complete circuit such that energy from energy source 990 (not shown) is applied to needle 24. Actuator 48 of device 10 shown in FIG. 12a is disengaged and actuator 48 shown in FIG. 12b is engaged. Activating switch 90 may also complete a circuit allowing energy to be supplied to a pump (not shown). Pump may contain a reservoir 360 from which fluid may be pumped through external tubing 700 into tubing 42 within device to lumen (e.g., 38, 40, 22). Thus, ablative energy may be applied to needle 42 and fluid may be delivered to target tissue through a single action, namely engaging actuator 48. As discussed below, needle 24 may also be deployed by engaging actuator 48

Needle delivery portion 52 of actuator 48 is coupled to proximal end 26 of needle 24 and is adapted cause the distal portion of the needle to extend into a target tissue. In the embodiment shown in e.g. FIG. 4 needle delivery portion 52 of actuator 48 may be coupled to block 64, which is coupled to proximal end 26 of needle 24. As shown in, e.g., FIG. 4, block 64 is slidably mounted in block guiding member 66 of housing 12. Block 64 comprises extensions 68. Block guiding member 66 is configured to receive extension 68 of block 64. Actuator 48 comprises block extension receiver 70, which is configured to receive extension 68 of block 64. When actuator 48 is engaged (e.g. FIG. 5), block 64 slides within housing 12 causing needle to slide through passageway 22 of elongate probe member 14. When actuator 48 is fully engaged (e.g. FIG. 5), distal end 28 of needle exits opening 72 of elongate probe member 14. While not shown in e.g. FIGS. 4-6, it will be understood that sheath 30 may also be coupled to needle delivery portion 52 of actuator 48. Sheath 30 may be coupled to block 64 as shown in e.g. FIG. 4 with regard to needle 24.

Figure 5:
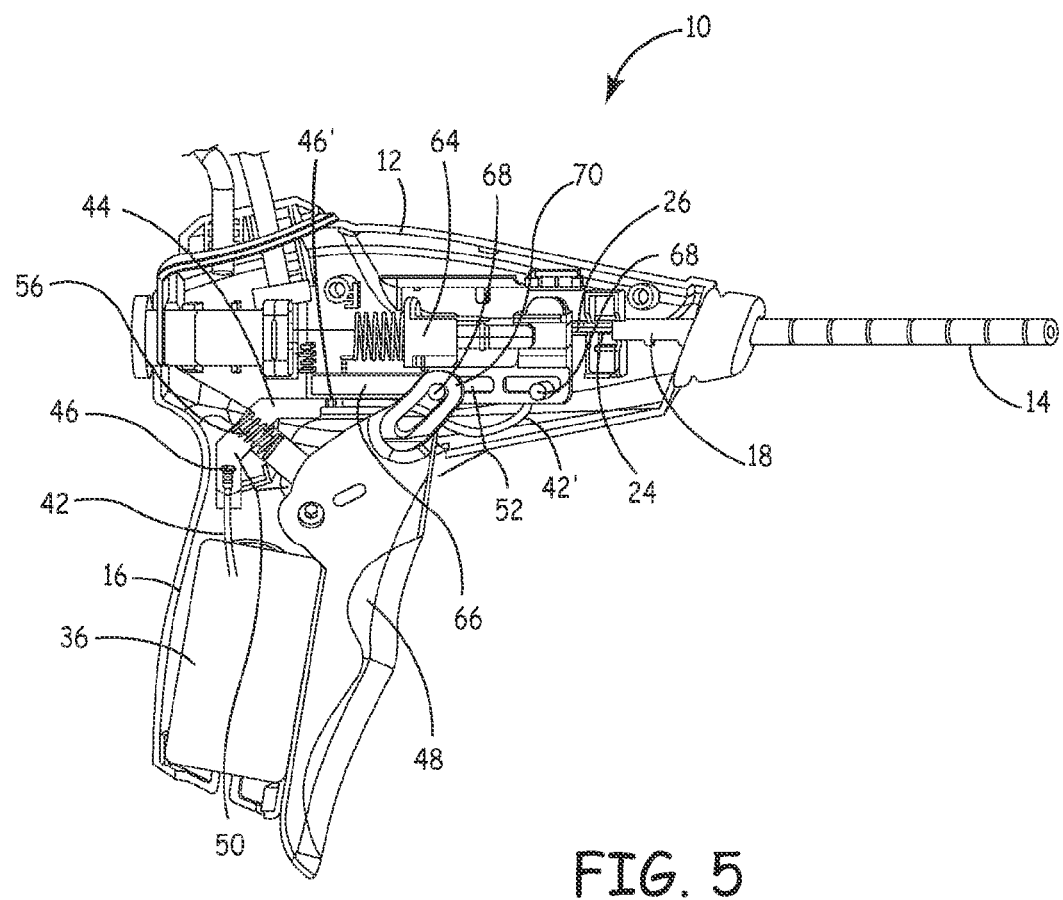
FIG. 5 is a diagrammatic illustration of a view of a partially exposed view of a device as in FIG. 4, wherein the actuator is engaged.

The actuator 48, as shown in e.g. FIG. 4, is disengaged. The actuator, as shown in e.g. FIG. 5, is engaged. Engaging the actuator 48 causes the distal portion of the needle to extend into a target tissue. Engaging the actuator 48, in various embodiments, may also cause fluid to flow through one or more of needle lumen 38, sheath lumen 40, and/or passageway 22 to target tissue location.

Figure 8:
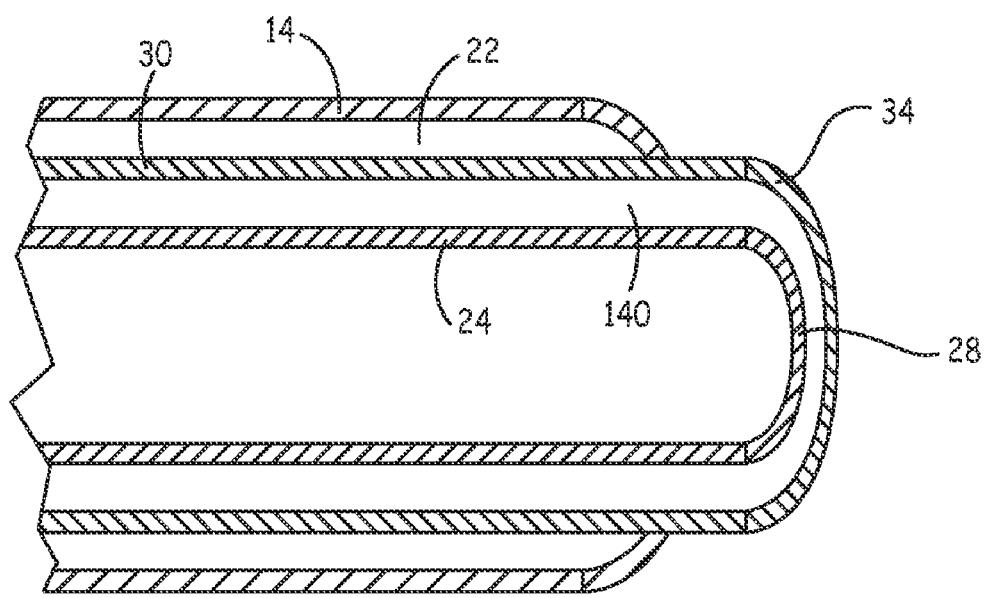
FIG. 8 is a diagrammatic illustration of a longitudinal section of a portion of a device as in FIG. 5.

FIGS. 7 and 8 depict a longitudinal section of elongate probe member 14 corresponding to a section to the right of line 240 in FIG. 4. While FIG. 4 does not depict a sheath 30, FIGS. 7 and 8 do depict a sheath 30, which is slidably disposed within passageway 22 of probe member 14. Needle 24 is slidably disposed within lumen 40 of sheath 30. Referring to FIG. 7, the needle 24 is retracted (i.e., the distal end 28 of needle 24 is within the confines of passageway 22), and the actuator 48 (not shown) is disengaged. Referring to FIG. 8, the needle 24 is deployed (i.e, extending through the opening 72 of passageway 22), and the actuator 48 (not shown) is engaged. As shown in FIGS. 7 and 8, the actuator 48 (not shown) may be coupled to sheath 30 and be adapted to cause the distal end 34 of sheath 30 to extend through the opening 72 of passageway 22 into a target tissue. The sheath 40 may be at least partially retracted (not shown) prior to applying ablative energy to the tissue location via the needle electrode 24. The one or more needle electrodes 24 may be coupled to an energy source 990 (not shown), such as an RF generator, such that ablative energy may be applied to the tissue through the needle 24.

Any medically acceptable conductive fluid may be delivered from device 10 to conductive fluid. As used herein, "conductive fluid" means a fluid capable of increasing conductivity of a tissue in which the fluid is placed. For example, a conductive fluid may be a solution comprising an ion capable of enhancing the conductivity of a tissue. The solution may comprise a cation having a charge of, e.g., +1 to +3 and/or may comprise an anion having a charge of, e.g., −1 to −3. A conductive fluid may be a solution comprising a salt. Any medically acceptable salt may be employed according to various embodiments of the invention. By way of example, a suitable salt may comprise sodium, potassium, calcium, and/or magnesium as a potential cation and may contain chloride, nitrate, nitrite, sulfate, phosphate, sulfate, and/or carbonate as a potential anion. The salts may be monobasic, dibasic, triba-sic, etc. Specific exemplary salts include $NaCl$, $CaCl_2$, $MgCl_3$, $KMgCl_3$, $Na_2SO_3$, $CaSO_4$, $MgSO_4$, $Na_2HPO_4$, $Ca_{10}(PO_4)_6$, $Mg_3(PO_4)_2$, $NaHCO_3$, $CaCO_3$, $MgCO_3$, $CaMgCO_3$, $NaNO_3$, $NaNO_2$, $KCl$, $KNO_3$, and $KNO_2$. Reference to a salt herein is intended to refer to anhydrous and hydrated forms of the salt.

A conductive fluid may comprise any concentration of a salt capable of increasing conductivity of a tissue in which the fluid is placed. In an embodiment, the conductive fluid comprises a salt concentration of about 0.9% by weight or greater. In an embodiment the conductive comprises a salt concentration of between about 0.9% and about 35% by weight.

Any amount of conductive fluid capable of increasing the conductivity of a target tissue may be delivered from device 10 to target tissue. In an embodiment, greater than about 0.1 cc of conductive fluid is delivered. In an embodiment, between about 0.1 cc to about 5 cc of conductive fluid is delivered.

An embodiment of the invention provides a method for ablating tissue at a target location. The method comprises introducing an electrode into the target location and introducing a conductive fluid to the target location. As used herein, "target location" means tissue to be ablated and tissue in proximity to the tissue to be ablated. The electrode and the conductive fluid are introduced into the target location through a single step carried out by a user of a system capable of introducing the electrode and the conductive fluid. The method further comprises applying energy to the target location via the electrode to ablate the tissue.

The single step of introducing the electrode and the conductive fluid may comprise engaging an actuator 48, as e.g. described above. The actuator 48 may be in the form of a trigger capable of being pulled by a human hand, as e.g. described above. Alternatively, the actuator may be in the form of a button, slide, switch, or any other means capable of causing an electrode to be introduced into a target location and capable of causing conductive fluid to be delivered to the target location. The actuator 48 may be operatively coupled to the electrode 24 and a supply housing the conductive fluid. The supply may be a reservoir 36, as e.g. described above. In an embodiment, a needle 24 comprises the electrode and the electrode is introduced by moving the needle.

In an embodiment, engaging the actuator causes the needle to be introduced to the target location and causes conductive fluid to flow from a supply housing the conductive fluid to the target location. Any means for causing the conductive fluid to flow from the supply to the target location may be employed. In an embodiment, engaging the actuator increases pressure in a supply housing the conductive fluid, forcing the conductive fluid to be discharged from the supply and directed to a target location. In an embodiment, engaging the actuator decreases pressure upstream the supply housing the conductive fluid, relative to the supply, causing the conductive fluid to be drawn from the supply towards the target location. In an embodiment, engaging the actuator opens a valve allowing the conductive fluid to flow to the target location. The valve is in fluid communication with the source of conductive fluid and has an open position and a closed position. The open position allows flow of the conductive fluid to the target tissue and the closed position prevents flow of the conductive fluid to the target tissue. The conductive fluid may be delivered under substantially constant pressure and/or at a substantially constant rate, such as when delivered by a pump.

Devices 10 according to the teachings of various embodiments of the invention may be used to ablate any tissue in a subject, such as a human patient, in need thereof. For example, prostate tissue may be ablated, tumors may be ablated, cardiac tissue may be ablated, skin tissue, kidney tissue, bladder tissue including tissue of the bladder neck, etc. Accordingly, various diseases or disorders may be treated using a device 10 capable of delivering a conductive fluid to a target tissue and extending needle electrodes 24 to a target tissue in a single action according to the teachings of various embodiments of the invention. In general, any disease or disorder of a subject that may benefit from ablation of a tissue may be treated. For example, hyperplasia, such as benign prostatic hyperplasia, stress incontinence, skin wrinkles, or cancer may be treated.

Various embodiments of the invention are disclosed. One skilled in the art will appreciate that embodiments other than those disclosed are contemplated. One of skill in the art will also appreciate that one or more element of one or more embodiment described herein may be combined to produce an apparatus or method in accordance with the teachings disclosed herein. The disclosed embodiments are presented for purposes of illustration and not limitation, and the present invention is limited only by the claims that follow.

All printed publications, such as patents, patent applications, technical papers, and brochures, cited herein are hereby incorporated by reference herein, each in its respective entirety.

What is claimed is:

1. A method for ablating tissue at a target location, comprising:
    introducing an electrode into a target tissue location;
    introducing a conductive fluid into the target tissue location; and
    ablating the target tissue by applying energy to the target tissue via the electrode, wherein the electrode and conductive fluid are introduced to the target location through a single step carried out by a user of a system capable of introducing the electrode and the conductive fluid, and wherein introducing the conductive fluid comprises opening a valve.

2. The method of claim 1, wherein the single step is engaging an actuator.

3. The method of claim 2, wherein introducing the electrode into the target tissue location comprises extending the electrode from a housing coupled to the actuator, and wherein engaging the actuator comprises engaging a trigger mechanism.

4. The method of claim 2, wherein introducing the electrode comprises introducing a needle comprising the electrode.

5. The method of claim 4, wherein engaging the actuator causes the needle to be introduced to the target location and causes conductive fluid to flow from a supply housing the conductive fluid to the target location.

6. The method of claim 5, wherein engaging the actuator increases pressure in the supply housing the conductive fluid, forcing the conductive fluid to be discharged from the supply and introduced to the target location.

7. The method of claim 5, wherein engaging the actuator decreases pressure upstream of the supply housing the conductive fluid, relative to the supply, causing the conductive fluid to be drawn from the supply towards the target location.

8. The method of claim 5, wherein the actuator is operatively coupled to the needle and to the valve, the valve being in fluid communication with a source of the conductive fluid and having an open position and a closed position, wherein the open position allows flow of the conductive fluid to the target tissue and the closed position prevents flow of the conductive fluid to the target tissue, and engaging the actuator opens the valve allowing the conductive fluid to flow to the target location.

9. The method of claim 8, wherein the conductive fluid is delivered under substantially constant pressure to the target tissue.

10. The method of claim 9, wherein the substantially constant pressure is provided by a pump.

11. The method of claim 1, wherein the energy is radio frequency energy.

12. The method of claim 1, wherein the conductive fluid comprises NaCl.

13. The method of claim 1, wherein opening the valve allows the conductive fluid to flow from a supply housing the conductive fluid, through the valve disposed within a housing, and to the electrode extending from the housing.

14. The method of claim 1, wherein opening the valve allows air to flow into a bladder that expands to pressurize the conductive fluid.

15. A method for ablating tissue at a target location, comprising:
    introducing an electrode into a target tissue location;
    introducing a conductive fluid into the target tissue location; and
    ablating the target tissue by applying energy to the target tissue via the electrode, wherein:
    the electrode and conductive fluid are introduced to the target location through a single step of engaging an actuator carried out by a user of a system capable of introducing the electrode and the conductive fluid;
    the actuator is operatively coupled to the needle and to a valve, the valve being in fluid communication with a source of the conductive fluid and having an open position and a closed position;
    the open position allows flow of the conductive fluid to the target tissue and the closed position prevents flow of the conductive fluid to the target tissue; and
    engaging the actuator opens the valve allowing the conductive fluid to flow to the target location.

16. The method of claim 15, wherein the conductive fluid is delivered under substantially constant pressure to the target tissue.

17. The method of claim 16, wherein the substantially constant pressure is provided by a pump.

* * * * *